(12) United States Patent
Frock et al.

(10) Patent No.: US 11,998,249 B2
(45) Date of Patent: Jun. 4, 2024

(54) INSTRUMENT FOR INSERTING AN INTERSPINOUS PROCESS IMPLANT

(71) Applicant: Spinal Simplicity, LLC, Overland Park, KS (US)

(72) Inventors: Melissa Frock, Lenexa, KS (US); Adam Frock, Lenexa, KS (US); Todd Moseley, Olathe, KS (US); Harold Hess, Leawood, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 17/949,648

(22) Filed: Sep. 21, 2022

(65) Prior Publication Data

US 2023/0240725 A1 Aug. 3, 2023

Related U.S. Application Data

(63) Continuation of application No. 17/587,666, filed on Jan. 28, 2022.

(51) Int. Cl.
*A61B 17/70* (2006.01)
*A61B 17/00* (2006.01)
*A61B 17/88* (2006.01)

(52) U.S. Cl.
CPC ...... *A61B 17/7065* (2013.01); *A61B 17/7062* (2013.01); *A61B 17/7074* (2013.01); *A61B 17/8883* (2013.01); *A61B 17/8891* (2013.01); *A61B 2017/00526* (2013.01)

(58) Field of Classification Search
None
See application file for complete search history.

(56) References Cited

U.S. PATENT DOCUMENTS

| 2004/0147937 | A1* | 7/2004 | Dunbar, Jr. | A61B 17/7086 606/99 |
| 2010/0234889 | A1* | 9/2010 | Hess | A61B 17/7071 606/279 |
| 2014/0257194 | A1* | 9/2014 | Edhouse | A61M 5/31553 604/198 |
| 2017/0296238 | A1* | 10/2017 | Snell | A61B 17/7082 |

* cited by examiner

*Primary Examiner* — Tessa M Matthews
(74) *Attorney, Agent, or Firm* — Erise IP, P.A.

(57) ABSTRACT

An insertion device for deploying an implant includes an elongated main body having a distal locking portion for coupling to the implant and a proximal handle portion. The main body defines a central passage and the distal locking portion has outer ridges and slots to allow the outer ridges to flex radially inward when mounting to the implant. A plunger slides in the central passage for movement between an unlocked position for mounting the implant on the distal locking portion, a locked position for locking the implant on the distal locking portion, and an insertion instrument deployed position for deploying the actuation plunger to move the blades from the stowed position to the deployed position. A spike cap drive rotatably mounts on the main body having a socket end for engaging a drive nut on the implant to, in turn, move the spike cap.

20 Claims, 22 Drawing Sheets

INSTRUMENT FOR INSERTING AN INTERSPINOUS PROCESS IMPLANT

CROSS-REFERENCE TO RELATED APPLICATIONS

This application is a continuation of U.S. patent application Ser. No. 17/587,666, filed Jan. 28, 2022, which is incorporated herein by reference in its entirety.

BACKGROUND OF THE INVENTION

Field of the Invention

The subject technology is directed to instruments for inserting spinal implants, and more particularly, to an insertion instrument that is easily assembled and disassembled for required cleaning while being able to effectively deploy an interspinous process implant for spinal stabilization, for percutaneous placement in a target interspinous process space, wherein the implant can also serve as a fusion cage spacer to treat lumbar spinal stenosis.

Description of Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not and thus turn to surgical treatment. Some surgical procedures for treating spinal stenosis are decompressive laminectomy and interspinous process decompression (IPD). A well-known implant used for performing IPD surgery is the X-STOP® device, which is described in U.S. Pat. No. 6,419,676, the disclosure of which is herein incorporated by reference in its entirety. Another interspinous process implant placed in a minimally invasive surgical procedure is disclosed in U.S. Patent Application Publication 2008/0243250, which is also incorporated herein by reference in its entirety.

Still another interspinous process implant placed in a minimally invasive surgical procedure is disclosed in U.S. Patent Application Publication 2010/0234889, which is also incorporated herein by reference in its entirety. One aspect of effective insertion of these implants is to provide a low profile instrument for deploying the implant. Often, the insertion instrument has several moving parts. Because of the cost of the insertion instruments, the instruments are re-used many times. For such insertion instruments to be re-used, the insertion instruments must be properly and fully cleaned without damage or loss of the components.

SUMMARY OF THE INVENTION

It would be advantageous to provide an insertion instrument for deploying spinal implants that can be easily disassembled for cleaning and assembled for use.

In one embodiment, the subject technology is directed to an insertion device for a spinal implant, wherein the spinal implant includes: a) an elongated body to function as a spacer placed in a target interspinous process space between two adjacent spinous processes, wherein the body defines an interior and a proximal internal recess for access to the interior, the proximal internal recess forming a transverse groove; b) a distal anchor that is at least partially threaded and has opposing radially deployable blades mounted for rotation about a pin transversely mounted in the interior; c) a proximal anchor including a spike cap mounted to slide along the body and a drive nut mounted for longitudinal movement along the body between a first position spaced apart from the distal anchor and a second position relatively closer to the distal anchor to thereby compress the two adjacent spinous processes between the spike cap and the distal anchor; and d) an actuation plunger slidably inside the interior for moving the blades from a stowed/insertion position to an implant deployed position.

The insertion device includes an elongated main body having a distal locking portion for coupling to the implant and a proximal handle portion. The main body defines a central passage and the distal locking portion has outer ridges. The at least one slot allows at least one of the outer ridges to flex radially inward. A plunger slides in the central passage for movement between an unlocked position for mounting the implant on the distal locking portion, a locked position within the slot for locking the implant on the distal locking portion, and an insertion instrument deployed position for deploying the actuation plunger to move the blades from the stowed position to the deployed position. A spike cap drive rotatably mounts on the main body having a socket end for engaging the drive nut to, in turn, move the spike cap.

Preferably, the insertion instrument includes a plunger stop coupled to the main body. The plunger stop has a central passage substantially aligned with the central passage of the main body, wherein: the plunger stop has a boss protruding into the central passage; and the plunger forms a three-part groove that captures the boss as the plunger slides and rotates within the central passage, the three-part groove having a first axial part that defines the unlocked position, an intermediate radial part that defines the locked position, and a second axial part that defines the insertion instrument deployed position. When the implant is mounted, in the unlocked position, the outer ridges are engaged in the transverse groove. In the locked position, the outer ridges are engaged in the transverse groove and the plunger extends through the central passage to be concentric with the outer ridges. In the insertion instrument deployed position, the plunger extends out of the central passage to move the actuation plunger of the implant.

As the size of the implant may vary, adapters are matched to the implant for coupling the socket end to the drive nut of the implant. The spike cap may also be keyed to the implant body to prevent rotation when driven. The implant has flat portions that allow efficient compression of the implant when engaged in the spinous processes.

In another embodiment, the subject technology is directed to an instrument for inserting an implant having a threaded body, selectively deployable distal blades, and a selectively deployable proximal anchor. The instrument includes an elongated main body having a proximal handle portion that defines a central passage and a distal portion that selectively couples to the implant. A plunger slides in the central passage to fix the implant to the elongated main body and deploy the distal blades. A spike cap drive is concentrically located about the plunger to deploy the proximal anchor. Preferably, the implant defines an interior with a transverse groove, the distal portion snaps into the transverse groove, and the plunger slides down central passage to prevent the distal portion from unsnapping from the transverse groove. The plunger can move between an unlocked position for mounting the implant on the distal portion, a locked position for locking the implant on the distal locking portion, and an insertion instrument deployed position for deploying the blade.

In still another embodiment, the subject technology is directed to an insertion instrument for inserting an implant having a body that defines a mounting recess. The insertion instrument includes an elongated main body having a proximal handle portion and a slotted distal portion that selectively couples to the mounting recess of the implant. A plunger slides in a central passage of the elongated main body for fixing the implant to the elongated main body by selectively filling the central passage within the slotted distal portion. Preferably, the implant defines an interior connected to the mounting recess. The implant may further include selectively deployable distal blades, and the plunger deploys the distal blades by extending out of the central passage into the interior.

The implant can further include a selectively deployable proximal anchor and the insertion instrument further comprises a spike cap drive concentrically located about the plunger and elongated main body to deploy the proximal anchor. The mounting recess may have a transverse groove so that the distal portion has ridges that snap into the transverse groove.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those skilled in the art to which the subject invention relates will readily understand how to make and use the insertion instrument of the subject technology without undue experimentation, embodiments thereof will be described in detail herein below with reference to the following figures.

DETAILED DESCRIPTION

Figure 1:
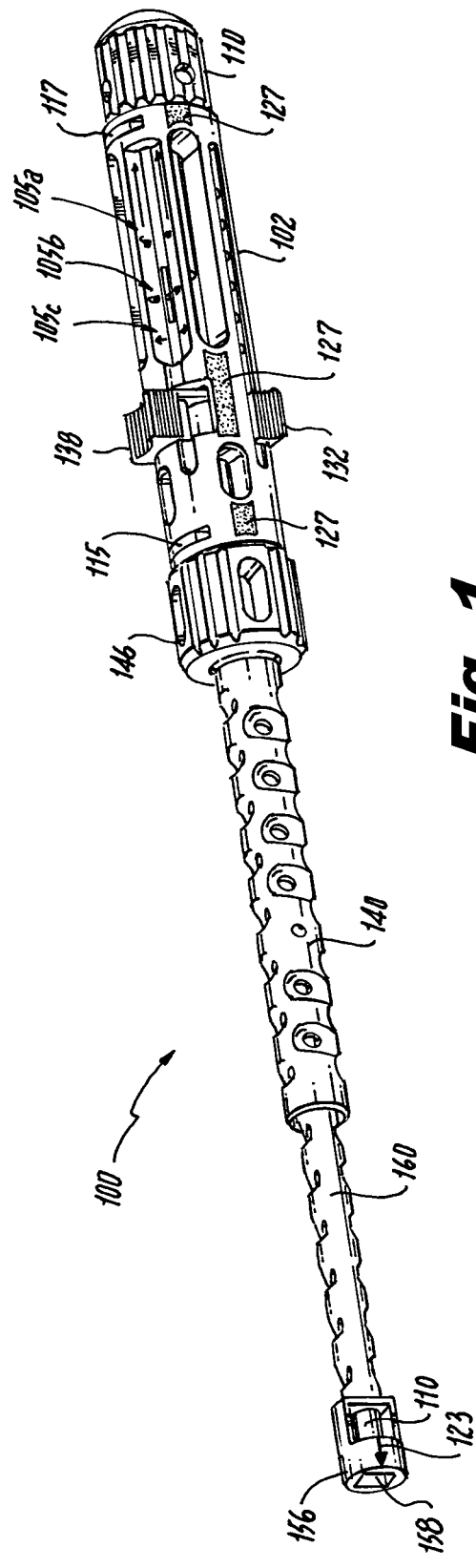
FIG. 1 is a perspective view of an insertion instrument in accordance with a first exemplary embodiment of the subject technology.

The present disclosure overcomes many of the prior art problems associated with instruments for inserting spinal implants and other devices such as cage spacers and the like. The advantages and other features of the instruments and methods disclosed herein will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as left, right, up, and down are with reference to the Figures, and not meant in a limiting sense. The illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed systems or methods. The shapes and sizes of components are also exemplary and unless otherwise specified, can be altered without materially affecting or limiting the disclosed technology.

Insertion Instrument

Figure 2:
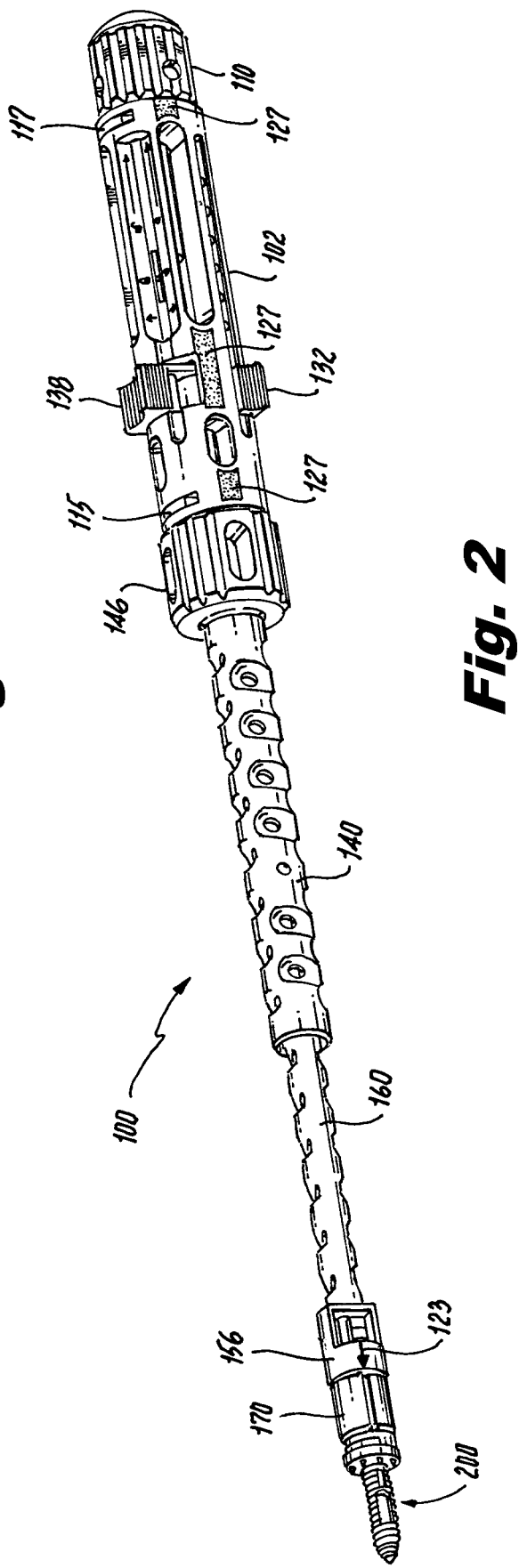
FIG. 2 is a perspective view of the insertion instrument of FIG. 1 with an implant in accordance with a first exemplary embodiment of the subject technology.

Referring now to FIG. 1, a perspective view of an assembled instrument 100 for inserting an implant in accordance with the subject technology is shown. The instrument 100 is particularly useful for inserting interspinous process implants and fusion cage spacers in accordance with those shown in U.S. PG Pub. No. 2010/0234889 (the '889 application). Referring additionally to FIG. 2, a perspective view of the insertion instrument 100 mounted with an implant 200 in accordance with the '889 application is shown.

After use, the instrument 100 can be disassembled easily to allow for full and proper cleaning, then reassembled to be used again. Preferably, the components of the instrument 100 are fabricated from medical grade stainless steel, alloys, and/or polymers (e.g., RULON, PEEK) or another like durable material to allow for repeated use, cleaning and reuse.

Figure 3:
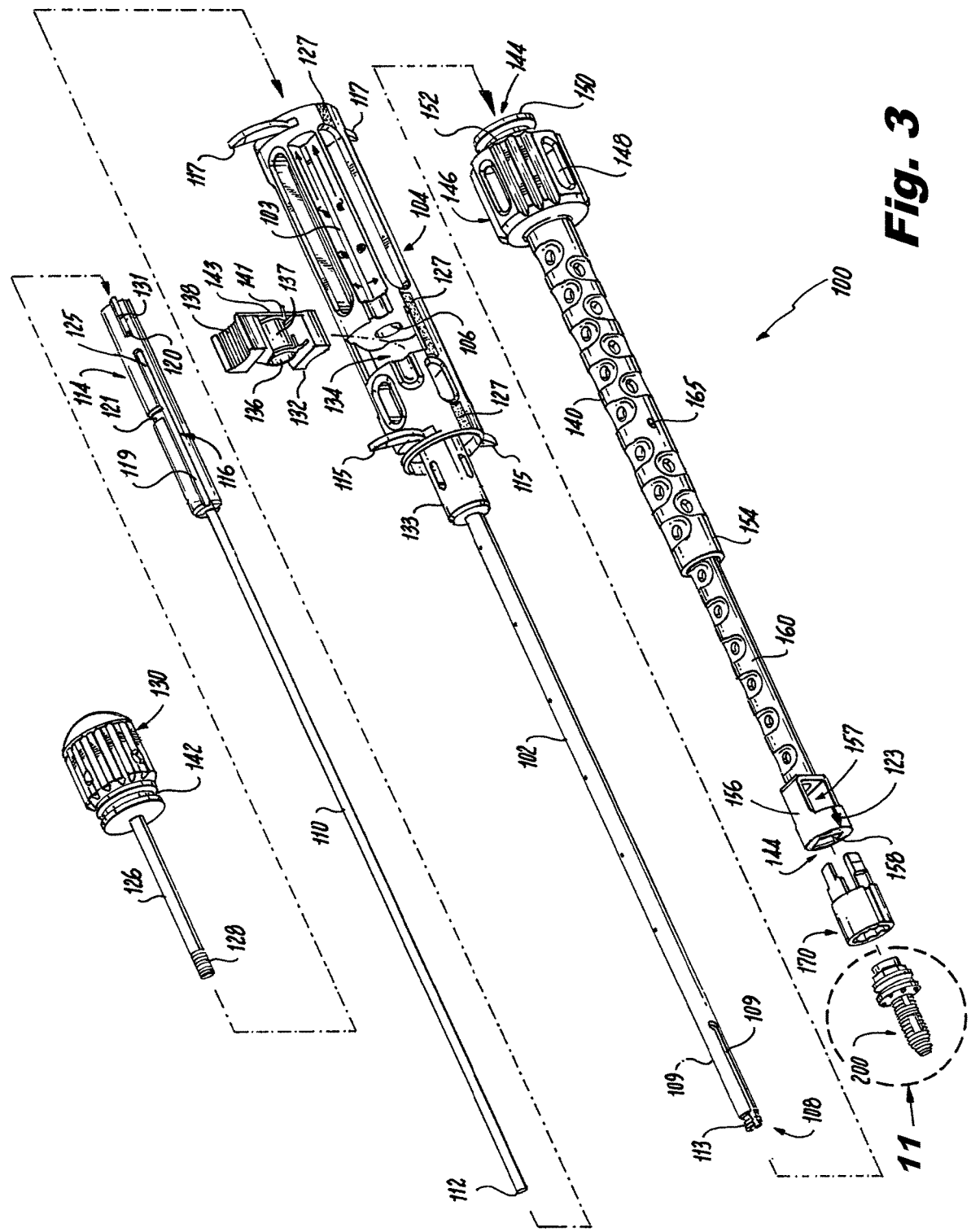
FIG. 3 is an exploded view of the insertion instrument of FIG. 1, illustrating the components thereof.

Referring to FIG. 3, an exploded view of the instrument 100 with an implant 200 is shown. The instrument 100 includes an elongated main body 102 having a proximal handle portion 104 that defines a central passage 106 and a distal portion 108 that selectively couples to the implant 200. The distal portion 108 forms axial slots 109 that allows compression of the tip 113. The tip 113 is roughly hexagonal shaped but as a result of the opposing slots 109, the tip 113 becomes two opposing, spaced apart "V" in cross-sectional shape. The tip 113 has four outer ridges 111, one ridge 111 on each flat section of the V-shape. The handle portion 104 also has stripes 127 to provide visual references to the user.

The handle portion 104 has a distal guide portion 133. The handle portion 104 of the main body 102 also has a first pair of opposing locking tabs 115. The locking tabs 115 are hingedly connected to the main body 102 to rotate radially inward and outward by the surgeon or surgical assistant. The handle portion 104 also has a second pair of opposing locking tabs 117 that are located relatively proximally compared to the first locking tabs 115. The second locking tabs 117 are also hingedly connected to the main body 102 to rotate radially inward and outward by the user. The handle portion 104 defines an axial recess 134. The axial recess 134 is formed by an angled surface 135 (best seen in FIG. 7).

Figure 23:
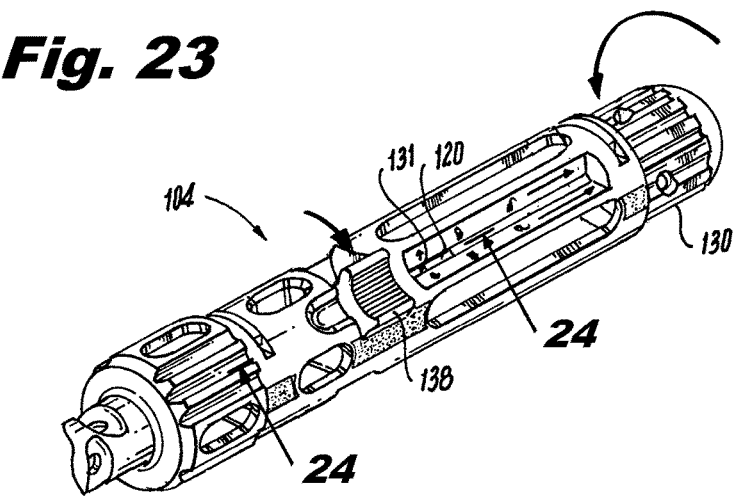
FIG. 23 is a perspective view of the insertion instrument with the plunger stop actuated to move the plunger from the locked to the deployed position.

The main body 102 also forms an axial wing slot 103 with location indicia 105a-c adjacent the wing slot 103 as described in more detail with reference to FIG. 23 among other figures herein. The indicia 105a-c combine with the reference notch 131 on the wings to indicate "unlocked," "locked" and "deployed" positions of the instrument 100, respectively, as described in more detail below. The main body 102 and spike cap drive 140 includes alignment indicia 123,127 in the form of stripes 127 and an arrow 123, respectively.

A plunger 110 slides in the central passage 106. The plunger 110 has a distal pushing end 112 and a proximal locking end 114. The proximal locking end 114 has a relatively thicker radius that includes a series of spaced apart radial holes 118. Opposing radial wings 120 are formed adjacent a proximal recess 122. The radial wings 120 include a reference notch 131. In FIG. 3, the plunger 110 is shown coupled to a plunger knob 126.

Figure 6:
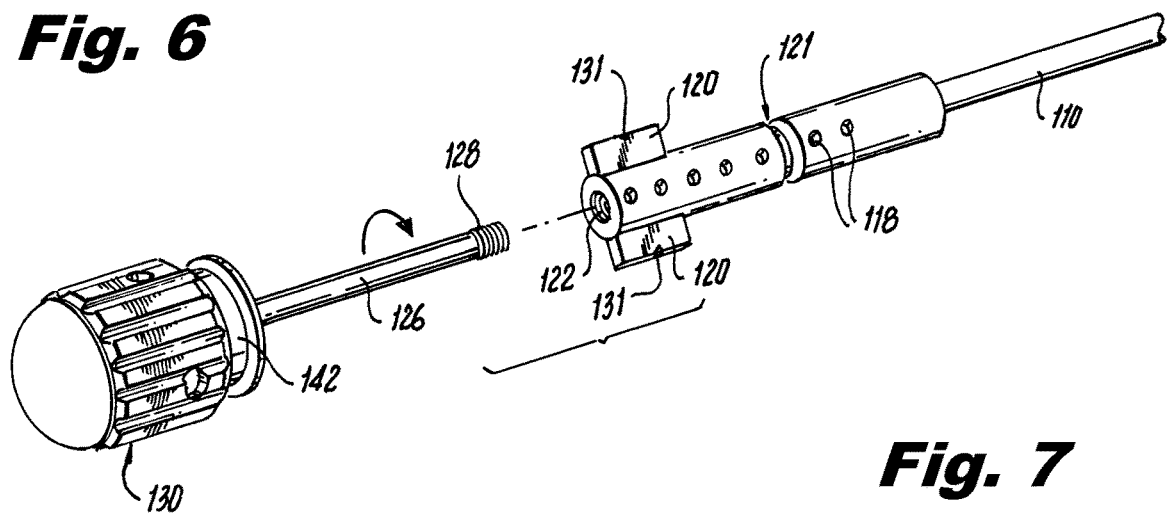
FIG. 6 is a further exploded view of the plunger and plunger knob of the insertion instrument of FIG. 1, illustrating the components thereof.

Referring now to FIG. 6, an exploded view of the plunger 110 and plunger knob 126 is shown. The proximal recess 122 has internal threads that are left-handed. The proximal locking end 114 also forms a three-part groove 116. The three-part groove 116 has a first distal axial groove portion 119 and a second proximal axial groove portion 125. Intermediate the groove portions 119, 125, the proximal locking end 114 forms a radial groove portion 121.

A plunger knob 126 has an externally threaded proximal end 128 that threadably couples to the axial threaded post 124 of the plunger 110. The plunger knob 126 has a proximal handle portion 130 for gripping to move the plunger 110 in the central passage 106. At the distal end of the handle portion 130, the plunger knob 126 has an annular recess 142 that extends completely around the plunger knob 126.

Figure 7:
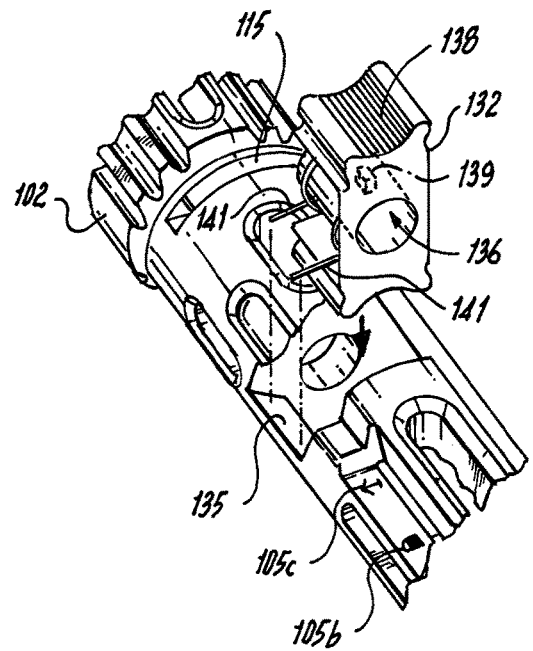
FIG. 7 is a perspective view of the plunger stop being coupled to the main body of the insertion instrument of FIG. 1.
Figure 9:
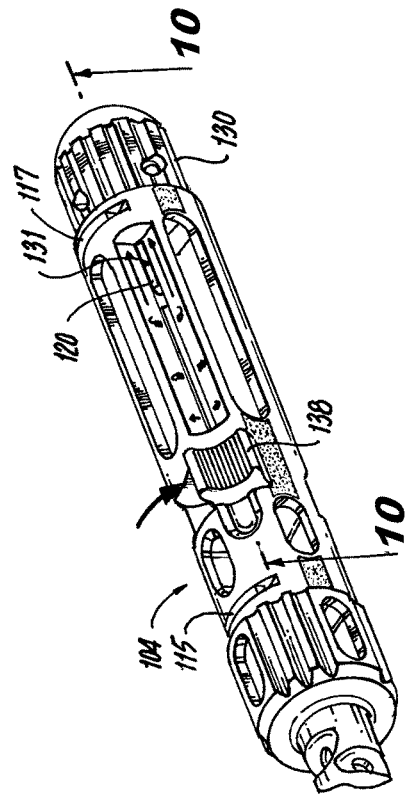
FIG. 9 is a perspective view of the assembled main body of the insertion instrument of FIG. 1.

Referring again to FIG. 3 as well as FIGS. 7 and 9, a plunger stop 132 seats in a recess 134 formed in the handle portion 104 of the main body 102 to guide the plunger 110 within the main body 102. The plunger stop 132 has two outer opposing lands 138 that facilitate a user holding the plunger stop 132 and manipulating position of the plunger stop 132 with their thumbs. The plunger stop 132 has tubular portion 137 that defines an axial passage 136 for receiving the plunger locking end 114. A boss 139, best seen in FIGS. 7 and 10, extends radially inward from the axial passage 136 to engage the groove 116 of the plunger locking end 114. A biasing spring 141 surrounds the tubular portion 137 such that ends 143 of the spring 141 extend outward.

Still referring to FIG. 3, a spike cap drive 140 defines an axial passage 144 for receiving the distal end 108 of the main body 102. The spike cap drive 140 has a proximal portion 146 that includes a relatively larger radius handle portion 148 with a smaller radius interlocking portion 150. The interlocking portion 150 defines an annular groove 152 for interacting with the main body 102. A tubular intermediate portion 154 extends from the handle portion 148 and slidingly receives a drive shaft 160. The drive shaft 160 terminates in a socket end 156. The socket end 156 is also tubular but forms a square opening 158 for coupling to the implant 200. The socket end 156 also forms a transverse square locking passage 157.

Figure 4:
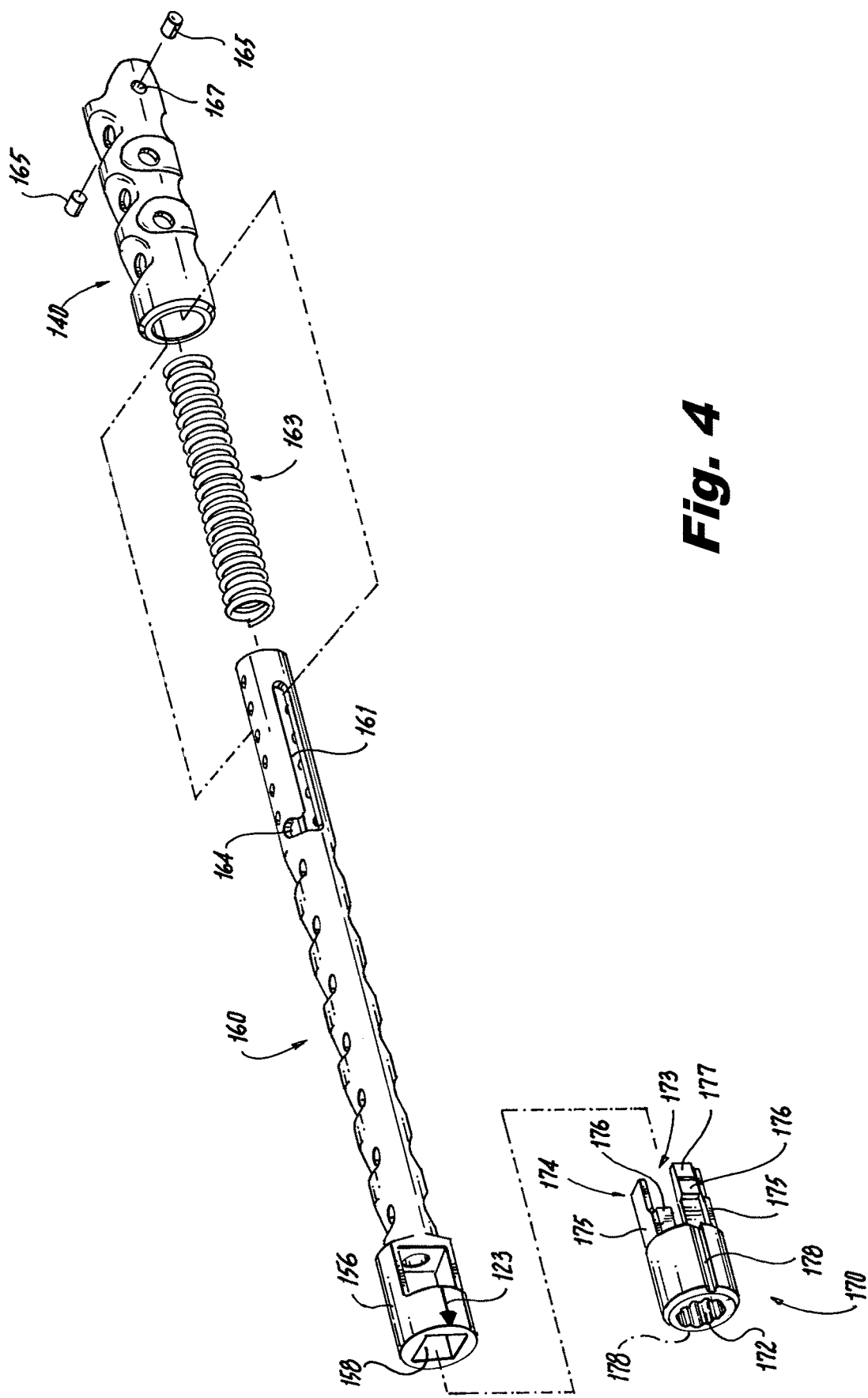
FIG. 4 is a further exploded view of the spike cap drive of the insertion instrument of FIG. 1, illustrating the components thereof.

The drive shaft 160 is also able to be locked in a retracted position within the intermediate portion 154. Referring now to FIG. 4, an exploded view of the spike cap drive 140 is shown. The spike cap drive 140 has a spring 163 mounted within the intermediate portion 154 for biasing the drive shaft 160 distally. So, in order to lock the drive shaft 160 in a retracted position, the bias of the spring 163 must be overcome. To accomplish this locking, the drive shaft 160 forms two opposing complementary slots 161 (only one slot 161 can be seen) and pins 165 mount in opposing pin holes 167 on the intermediate portion 154. When assembled, the pins 165 ride in the respective slots 161 so that upon fully pushing the drive shaft 160 in the intermediate portion 154, a small rotation of the drive shaft 160 will set the pins 165 in a radial portion 164 of the slots 161 and retain the spike cap drive 140 in this compressed position.

Referring again to FIG. 3, an adapter 170 attaches to the square opening 158 of the spike cap drive 140 to provide a hex socket 172 for coupling to the implant 200. The hex socket 172 can vary in size to accommodate different size implants 200. The adapter 170 has a central axial passage 173 to slide over the tip 113 of the main body 102. The adapter 170 has a standard male square open proximal end 174 to couple to the square opening 158. The proximal end 174 has two opposing rigid legs 175 intermediate two opposing flexible legs 176. Each of the flexible legs 176 has a locking tab 177 so that as the proximal end 174 is pushed into the square opening 158 of the spike cap drive 140, the legs 176 deflect to allow easy insertion, then the tabs 177 couple to the transverse locking passage 157 to securely retain the adapter 170 on the drive shaft 160. To remove the adapter 170, the locking tabs 177 are simply depressed while retracting the adapter 170. The adapter 170 also has opposing outer axial alignment ridges 178.

The Implant

The implant 200 may take a variety of different configurations and sizes. Preferably, the implant is useful for treatment of spondylolisthesis, central and foraminal lumbar stenosis, degenerative disc disease and the like. Beneficially, the implant 200 is percutaneously placed, provides stabilization of the spine, can be used with bone graft material to promote fusion, requires less than a 2.6 cm incision, and can be inserted with local or general anesthesia. As such, the recovery time is relatively quicker and the hospital stay is relatively shorter.

FIGS. 11-16 illustrate in detail the interspinous process implant 200 for use the with insertion instrument 100. The implant 200 includes a body 212, providing overall structure to the implant 200. The body 212, as illustrated, is provided with threads 222 for facilitating insertion of the implant 200 into a target interspinous process space 382 (FIGS. 20-22, 27, 28 and 30), as will be described in more detail below in connection with FIGS. 20-30, as well as for providing additional engagement with the anatomy of the patient in the target interspinous process space 382. Further, the threads 222 permit rotational engagement between the body 212 and a proximal nut 235, provided to securely engage the implant 200 with interspinous processes 381a, 381b adjacent the target interspinous process space 382, which will be described in more detail below. Alternatively, the implant 200 can be provided without threads thereon, or with threads provided only on a portion thereof for one of the foregoing functions. That is, if desired, threads 222 can be provided only on the proximal end of the body 212, for engaging the nut 235 and not on the distal portion, or vice versa.

The implant 200 include a distal anchor portion, which is configured as two opposed deployable blades 220 (220a, 220b). The blades 220 are provided with a common pivot, defined by a pin 259 passing therethrough, as well as through the body 212. Use of a common pivot advantageously minimizes the space required for housing all elements within the body 212 in their stowed state, although variations from this precise configuration are possible. For example, two separate pivots can be provided for each blade 220a, 220b, still in keeping with the invention. The blades 220, as illustrated, are provided with proximally directed spikes 224 for engaging the relevant adjacent bony anatomy, such as the spinous processes 381a, 381b. The blades 220 can alternatively be provided without such spikes 224.

In the illustrated embodiment, an implant plunger 226 is provided and includes a head portion 228 shaped and configured to act as a cam and cooperate with inner cam surfaces 240 formed on each of the blades 220a, 220b, as described above. As the plunger head 228 moves distally, cam surfaces 240 of the blades 220a, 220b follow the outer surface of the plunger head 228, and urge the blades 220a, 220b radially outwardly. In addition, the plunger 226 can include, as described above, a proximal head 225 having a proximal internal recess 221, and an angled distal surface to facilitate distally-directed urging and proximal-directed urging, respectively, applied from the proximal direction.

The blades 220a, 220b are respectively provided with hinge portions 223a, 223b for engaging the pin 259. In the illustrated embodiment, one hinge portion 223a is shaped as a clevis, while the other hinge portion 223b is shaped to fit within the clevis-shaped hinge portion 223a.

Preferably, the implant plunger 226 also includes a recess 229, for securely engaging a resilient catch 227. The catch 227 is configured to interface between the implant plunger 226 and internal surface features of the body 212, such as annular grooves or recesses 254. As described, the resilient catch 227 permits axial movement of the implant plunger 226, and in conjunction with the above-described internal surface features of the body 212, defined positions at which the implant plunger 226 is held, inhibiting unintentional movement therefrom. The catch 227 can be formed of any suitable material or configuration, such as from a resilient material, such as an elastomer, or as a resilient structure, such as a toroidal metallic coil, or a combination of these, for example. The catch 227 can be, in accordance with the invention, a canted coil, such as a Bal Latch™, available from Bal Seal Engineering, Inc. of Foothill Ranch, California, USA.

When deployed, the blades 220 function in concert with the spike cap 230, which is axially moveable along the length of the implant 200. The nut 235 includes threads on its inner surface that engage the threads 222 provided on the outer surface of the body 212. Accordingly, rotational movement of the nut 235 yields axial movement thereof. When that axial movement is in the distal direction, the nut 235 urges the spike cap 230 distally until the spike cap 230 abuts the bony structures (e.g. spinous processes 381a, 381b) surrounding the target interspinous process space 382. If provided, protrusions or spikes 234 on the proximal anchor portion facilitate engagement with the bone and thus stabilization of the entire vertebrae-implant construct.

As illustrated, opposed flat portions 217, comprising upper and lower flat portions 217a, 217b, respectively, guide correspondingly shaped (e.g., flat) portions 237 of the spike cap 230, permitting axial movement but inhibiting rotational movement thereof, during movement of the nut 235. A lock washer 233 or equivalent feature can be provided to inhibit unintentional loosening of the nut 235 following implantation and deployment of the blades 220a, 220b.

Figure 15:
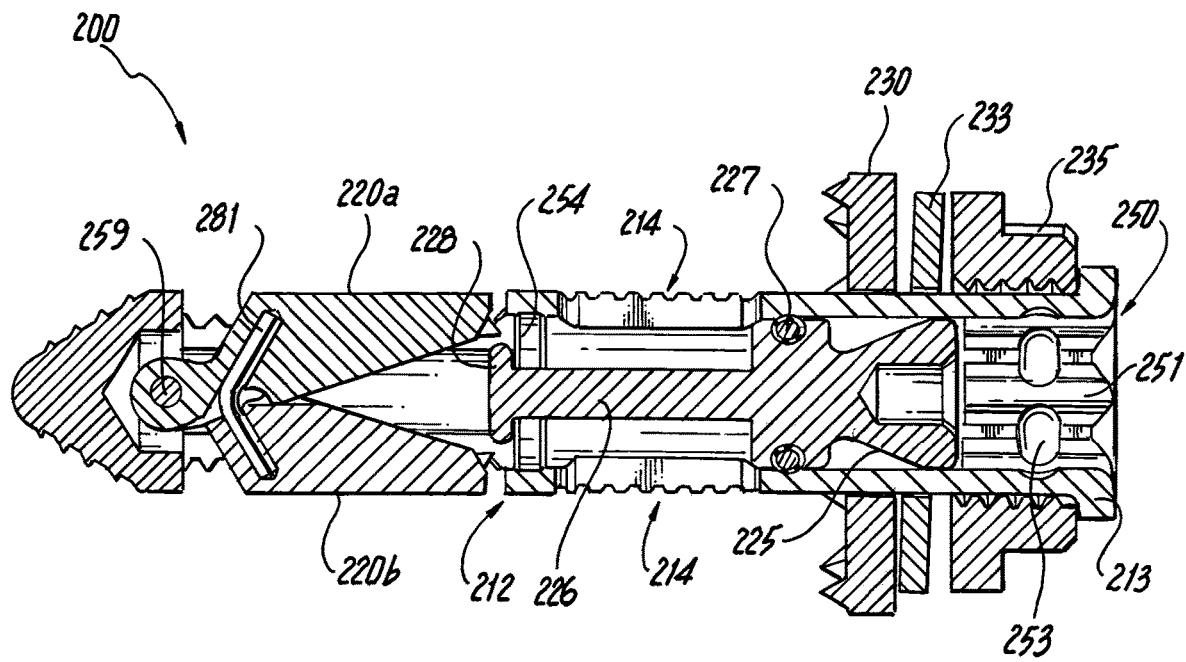
FIG. 15 is a cross-sectional view of the implant of FIGS. 11-14 taken at line 15-15 of FIG. 11, where the distal anchor elements are in a stowed position.
Figure 16:
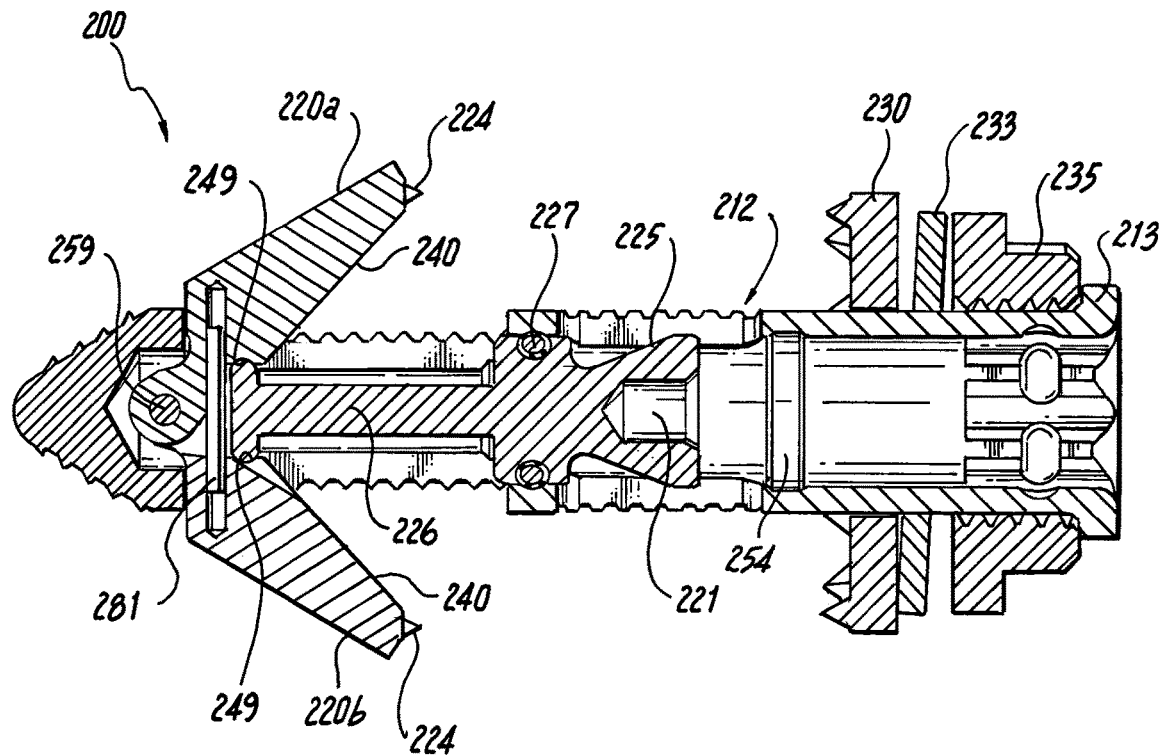
FIG. 16 is a cross-sectional view of the implant of FIGS. 11-14 taken at line 16-16 of FIG. 12, where the distal anchor elements are in a deployed position.

With reference to the cross-sectional views of FIGS. 15 and 16, in the illustrated embodiment, the blades 220 can be provided with an internal spring element 281, spanning between respective recess in each of the blades 220a, 220b. The spring element 281 can be provided straight to maintain the blades 220a, 220b deployed (open) normally, or alternatively, bent, to maintain the blades 220a, 220b stowed (contracted) normally. In accordance with one aspect, the spring element 281 is provided bent, and urges the blades 220a, 220b inwardly, toward the stowed position, prior to and during implantation. Thus, in connection with the implant plunger 226, the spring 281 serves to maintain a position of the blades 220. As illustrated, when the implant plunger 226 is fully extended, a head portion 228 thereof engages a corresponding detent 249 in the blades 220a, 220b. The engagement of the detent 249 by the head portion 228 further ensures secure deployment of the blades 220a, 220b.

The spring element 281 can alternatively be provided as normally straight, urging the blades 220a, 220b outwardly toward the deployed position, prior to, during and following implantation. During implantation, however, the spring element 281 permits inward rotation of the blades 220a, 220b, temporarily bending the spring element 281 in the process. Thus, during implantation the spring 281 serves to maintain a position of the blades 220a, 220b against externally-applied forces. Once placed in the target interspinous process space 382, the implant plunger 226 can be urged distally in order to lock the blades 220a, 220b in the deployed position. Engagement of the detent 249 by the head portion 228 of the implant plunger 226 further ensures maintenance of that position.

The body 212 of the implant 200 includes at its proximal end, an expanded-diameter portion 213, defining a proximal-most limit for traveling of the nut 235 and spike cap 230. Also in the proximal end portion, formed within the proximal internal recess 250, is a shaped socket 251 for engagement with the insertion instrument 100 as discussed in more detail below. As illustrated, the socket 251 is substantially hexagonal, with flat portions defined at regular angular intervals. Practicable departures from the precise configuration illustrated are possible. The shaped socket 251 facilitates mutual rotational engagement between the implant 200 and the insertion instrument 100.

Also provided in connection with the socket 251, are transverse grooves 253, which, in conjunction with the tip 113 of the main body 102 and pushing end 112 of the plunger 110 mount and lock the implant 200 to the insertion instrument 100. The mounting and/or locking elements on the insertion instrument can also be, for example, a resiliently and optionally lockable protrusion extending laterally (i.e., radially) from the insertion instrument. The lockable protrusion may be, for example, a lockable spring-loaded spherical element, for example.

The implant 200 can be provided with one or more apertures 214 to permit packing of the implant, such as in the proximal internal recess 250 thereof, with osteogenesis-promoting substances to facilitate bone ingrowth and/or fusion, such as demineralized bone.

Assembly of the Insertion Instrument

Figure 5:
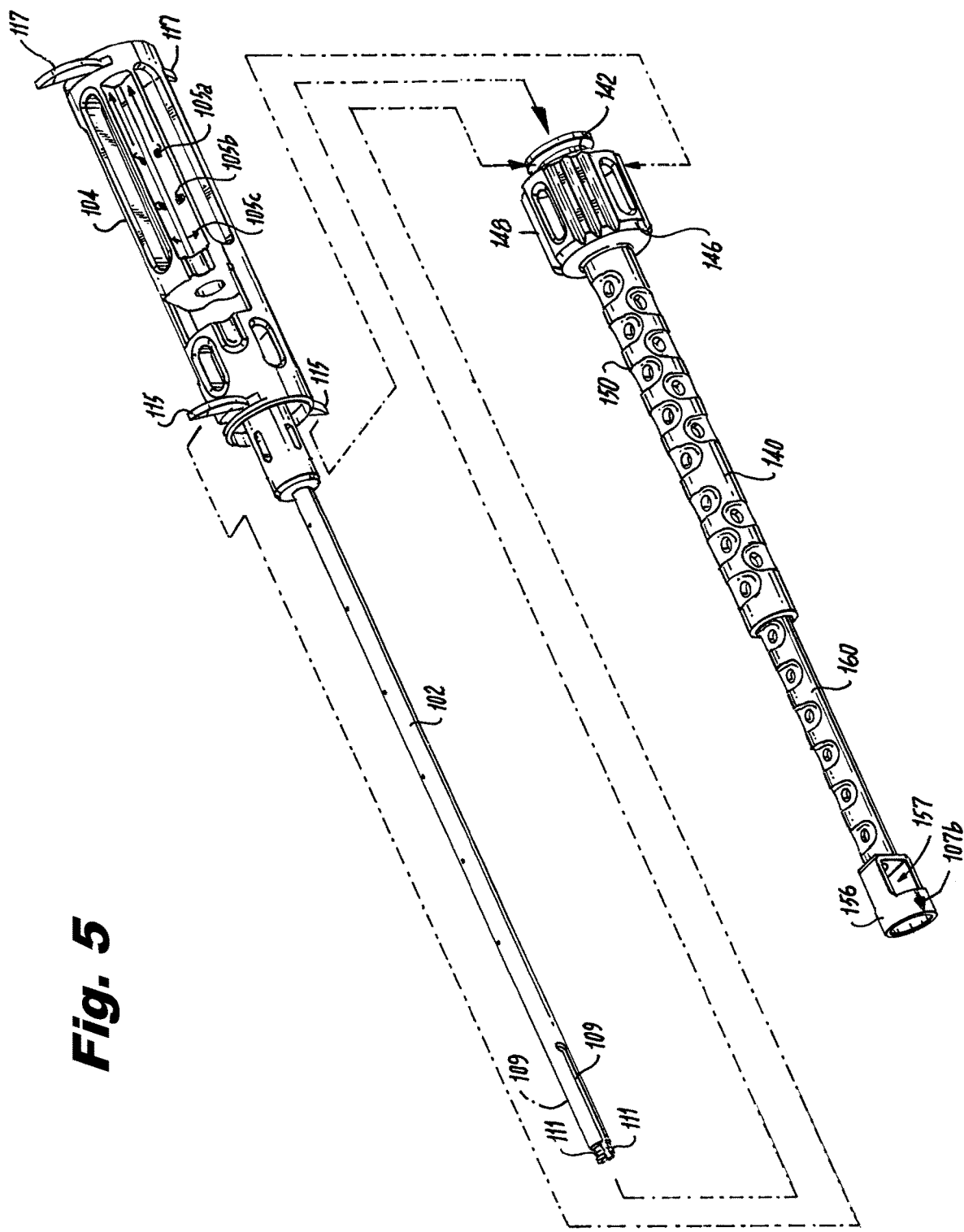
FIG. 5 is a perspective view of the main body ready to engage the spike cap drive of the insertion instrument of FIG. 1.

Referring now to FIGS. 3 and 5, in order to assemble the insertion instrument 100, the distal portion 108 of the main body 102 is inserted into the axial passage 144 of the spike cap drive 140 until the proximal handle portion 104 is flush against the handle portion 148 of the spike cap drive 140. The first locking tabs 115 are rotated from the open position shown in FIG. 5 to the closed position shown in FIG. 1. The first locking tabs 115 axially lock the main body 102 and the spike cap drive 140 together. The locking occurs by the locking tabs 115 extending into the annular groove 152 of the spike cap drive 140 and snapping fixedly into place. Preferably, the user hears an audible click to know that the engagement of the tabs 115 into the groove 152 has been fully completed. The spike cap drive 140 can still rotate with respect to the main body 102. The distal guide portion 133 of the main body 102 is sized so that the spike cap drive 140 rotates smoothly. A suitable material or coating may be used in contact areas to prevent wear and galling.

Figure 8:
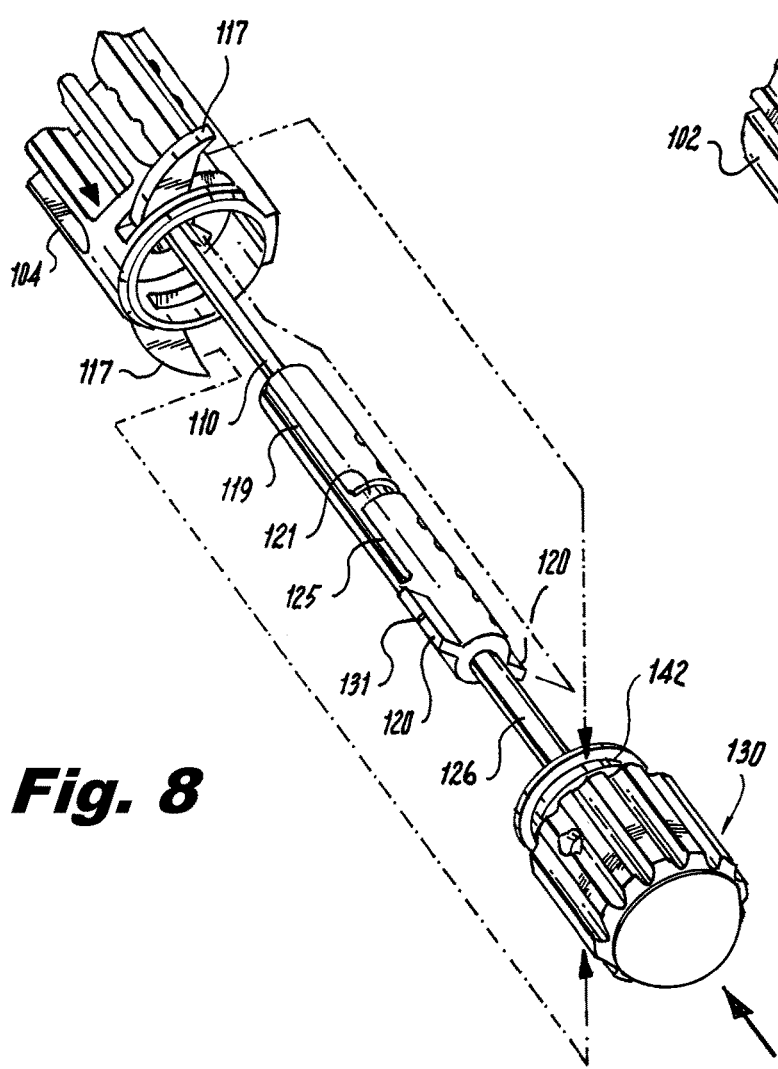
FIG. 8 is a perspective view of the plunger being coupled to the main body of the insertion instrument of FIG. 1.

Referring to FIGS. 6-8, the threaded distal end 128 of the plunger knob 126 is partially threaded into the recess 122 of the plunger 110 as shown in FIG. 6. The plunger knob 126 is turned counter-clockwise because the threading is left-handed. The plunger stop 132 is seated in the recess 134 of the main body 102 as shown in FIG. 7. The plunger stop 132 is seated with the ends 143 of the spring 141 against the angled surface 135 so that the plunger stop 132 will be biased for clockwise rotation when one looks down the insertion instrument 100 from the proximal to the distal direction.

While holding the plunger stop 132 in place with one hand, the plunger 110 can be partially inserted into the central passage 106 of the main body 102 by holding the plunger knob 126 with the other hand as shown in FIG. 8. As noted above, at this point, the plunger knob 126 need not be completely threaded into the plunger 110 but the plunger knob 126 may be. The radial wings 120 will slide in the slot 103 of the main body 102 so that the reference notch 131 is adjacent the indicia 105a-c.

Figure 10:
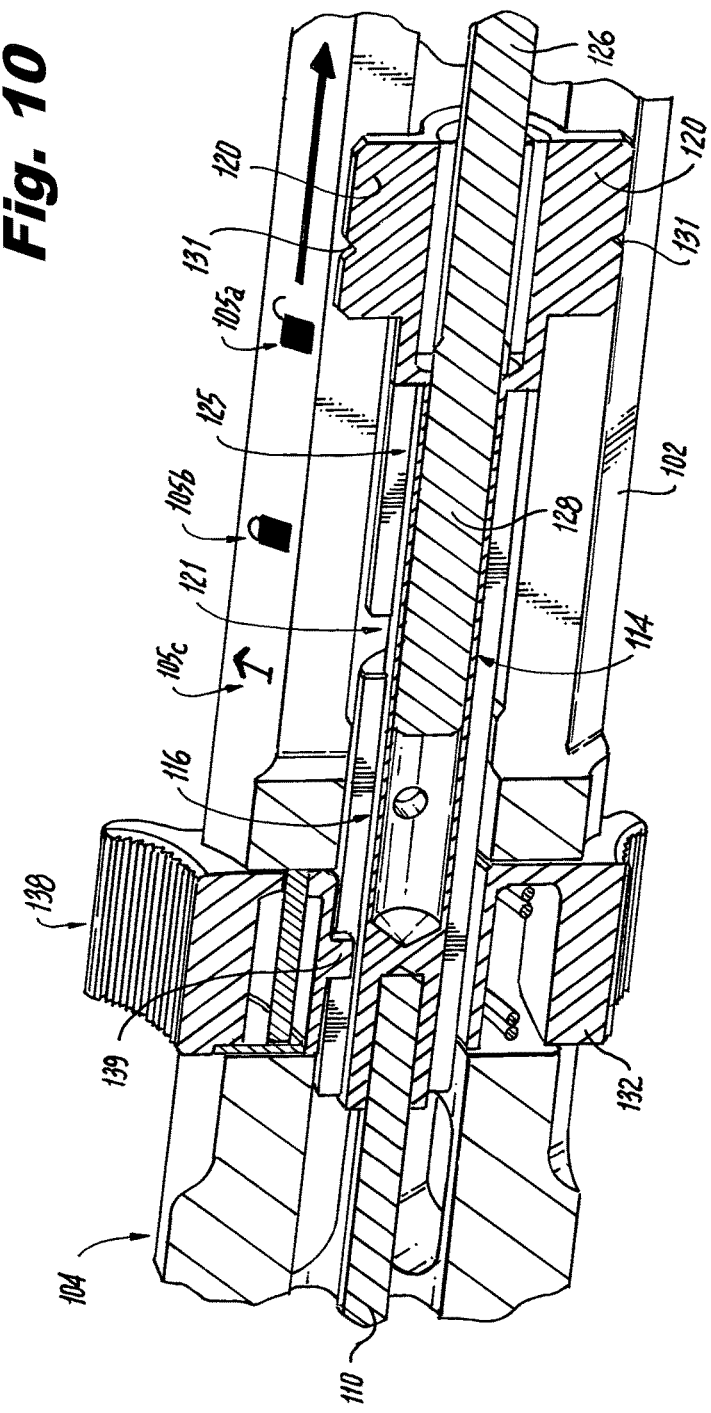
FIG. 10 is a cross-sectional view of the insertion instrument of FIG. 9 taken at line 10-10 of FIG. 9, where the plunger is an unlocked position.
Figure 11:
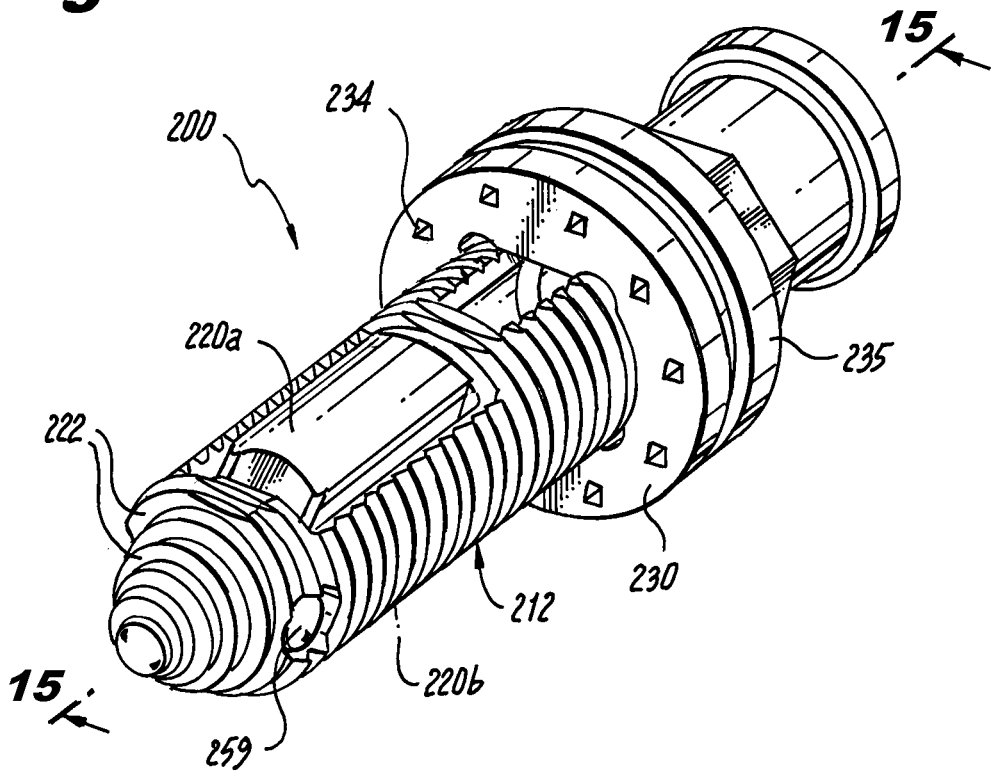
FIG. 11 is a perspective view of the implant with blades in a stowed position.
Figure 12:
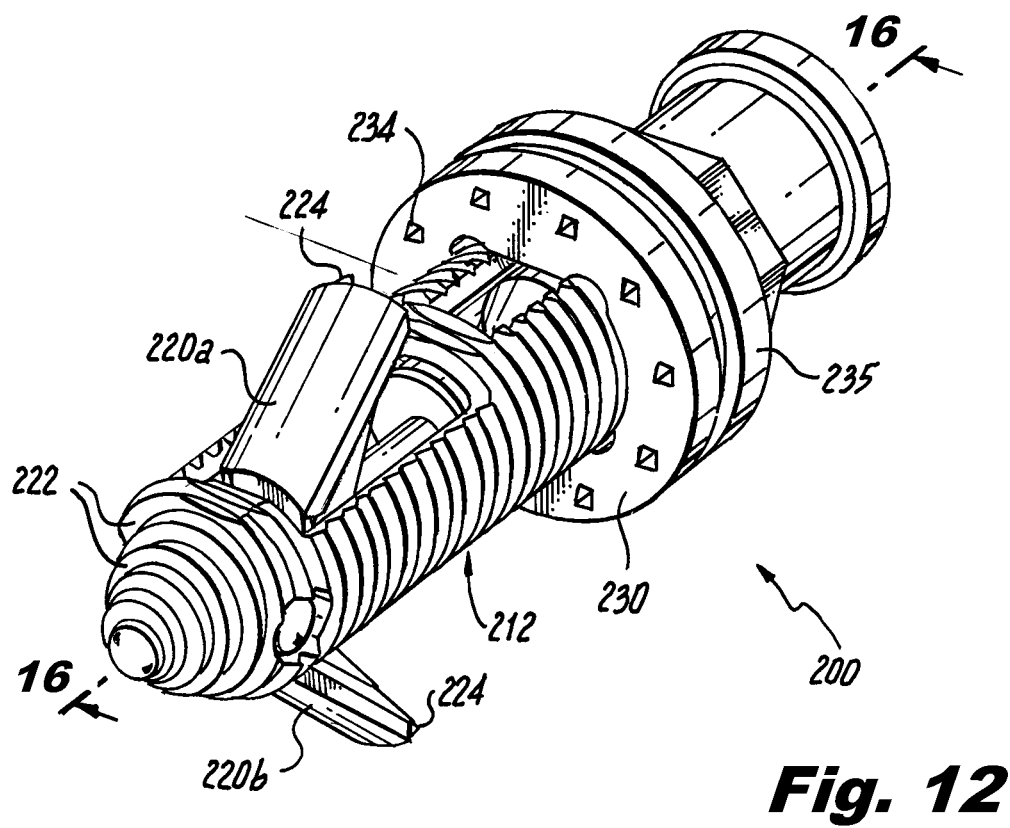
FIG. 12 is a perspective view of the implant with blades in a deployed position.
Figure 13:
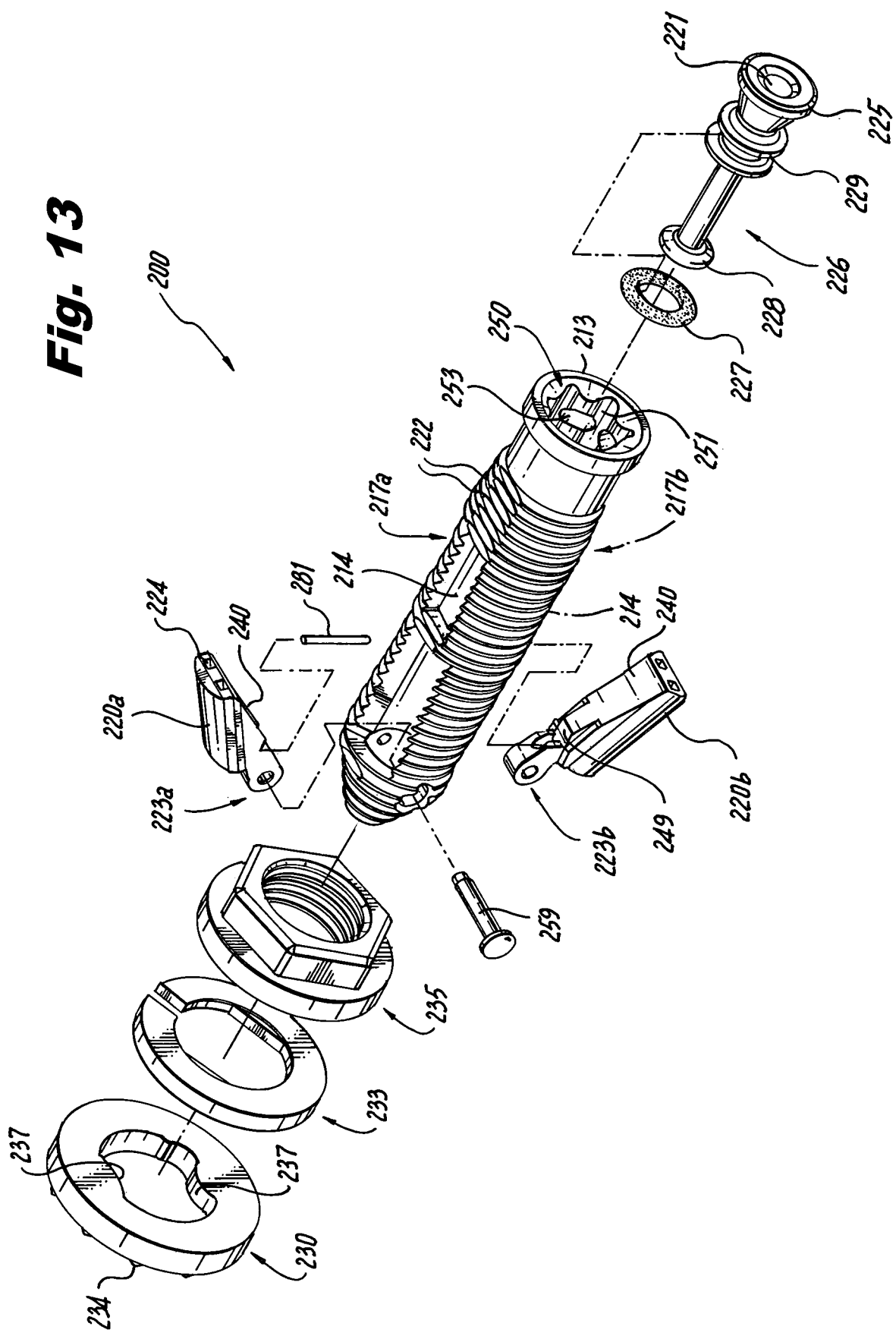
FIG. 13 is a rear exploded view of the implant in accordance with the subject technology.
Figure 14:
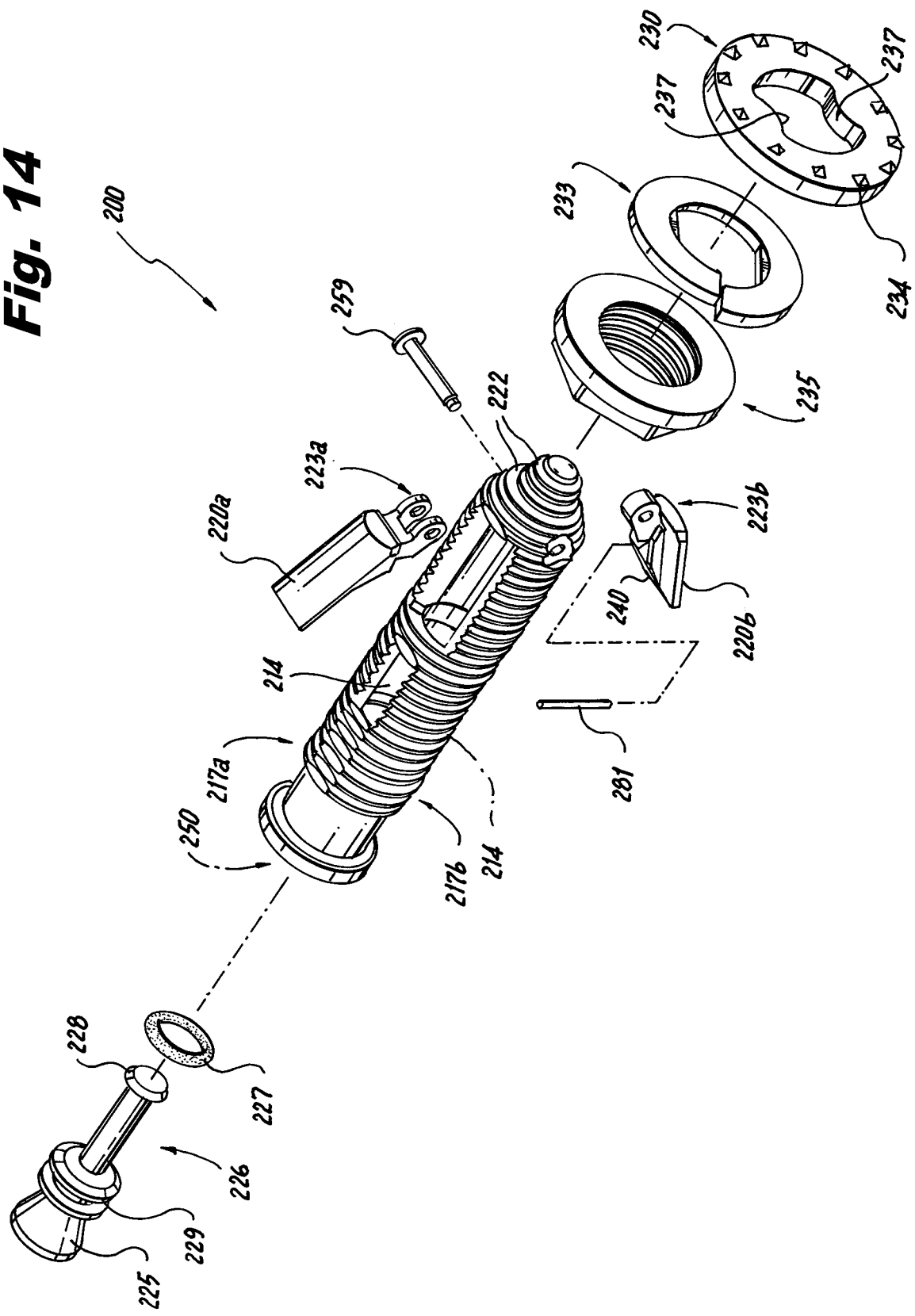
FIG. 14 is a front exploded view of the implant in accordance with the subject technology.

As the plunger 110 is inserted through the plunger stop 132, the user applies rotational force to the plunger stop 132 by using the thumb lands 138 to make sure that the plunger stop boss 139 aligns with the distal axial groove portion 119. The user must apply enough force to overcome the spring 141 because the spring 141 biases the plunger stop 132 in the axial groove portion 119 towards the radial groove portion 121. Once the plunger stop boss 139 is in the distal axial groove portion 119, as shown in FIG. 10, and the plunger knob 126 is flush against the proximal handle portion 104 of the main body 102, the second pair of opposing locking tabs 117 are clicked into the annular recess 142 of the plunger knob 126 as shown in FIG. 9. As a result, the plunger 110 and plunger knob 126 are axially locked to the main body 102.

Referring to FIG. 10, when the plunger stop boss 139 is in the first distal axial groove portion 119, rotation of the plunger 110 is prevented until the boss 139 reaches the radial groove portion 121 of the plunger 110. However, rotation of the plunger knob 126 is still possible.

While the boss 139 is in the axial groove portion 119 and both pairs of locking tabs 115, 117 are properly secured, the instrument 100 is in the "unlocked" position as visually indicated to the user by the reference notch 131 being adjacent the unlocked indicia 105a. "Unlocked" refers to the implant 200 not being secured to the insertion instrument 100 even if the implant 200 is mounted on the tip 113. The implant 200 is locked to the insertion instrument 100 by deploying the plunger 110 as described below.

Locking the Implant to the Insertion Instrument

As would be understood from the description above, even once assembled, several components of the insertion instrument 100 are able to move. Thus, it is important to make sure the moving components are in the proper position to be ready for mounting the implant 200. In particular, the plunger 110 should be fully retracted into the unlocked position by turning the plunger knob 126 counter clockwise while rotating and holding the plunger stop 132 to allow plunger 110 travel (i.e., the boss 139 of the plunger stop 132 is aligned with the first axial distal groove portion 119 of the plunger 110 as shown in FIG. 10). Once the plunger 110 is fully retracted, the reference notch 131 will indicate fully unlocked on the unlocked indicia 105a.

Turning to the selection of the implant 200, it is envisioned that the implant 200 comes in a variety of sizes so that an appropriate size can be selected for a desired amount of interspinous distraction. Any technique now known and later developed may be used to determine the proper interspinous distraction. Once the proper size implant 200 is selected, the corresponding or matching adapter 170 can be selected. Once the adapter 170 has been chosen, the implant 200 can be mounted on the insertion instrument 100.

Figure 17:
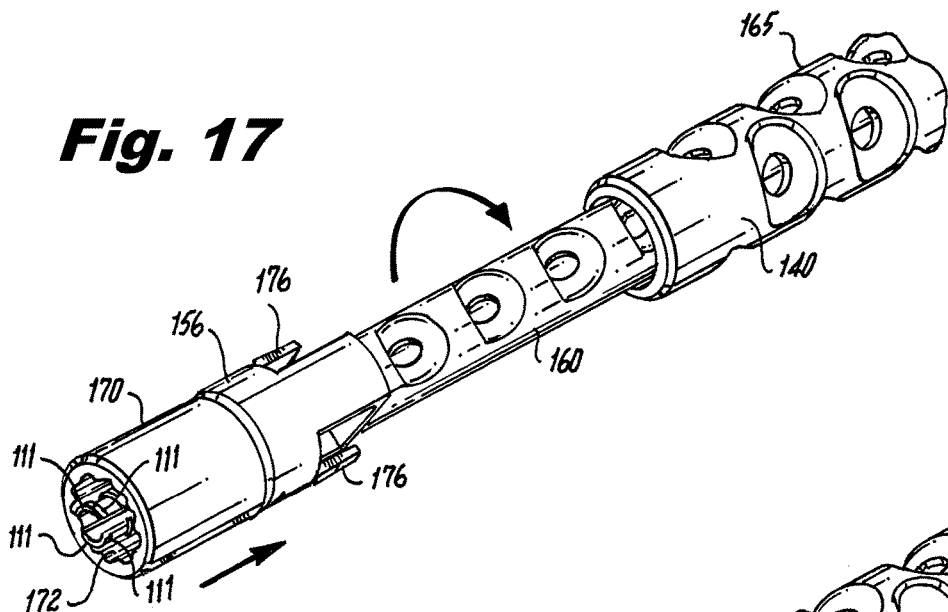
FIG. 17 is a perspective view of the spike cap drive being retracted from the distal tip of the main body of the insertion instrument of FIG. 1.

Referring now to FIG. 17, the distal portion 108 of the main body 102 is uncovered by sliding the drive shaft 160 into the intermediate portion 154 of the spike cap drive 140. The drive shaft 160 is initially prevented from rotation because the pins 165 are riding in the slots 161 (best seen in FIG. 4). However, once the pins 165 bottom out in the slots 161, the user can hold the handle portion 148 and rotate the drive shaft 160 so the pins 165 come to rest in the radial portion 164 of the slots 161. As a result, the drive shaft 160 is retained in the intermediate portion 154 and will stay retracted even when released by the user.

Figure 18:
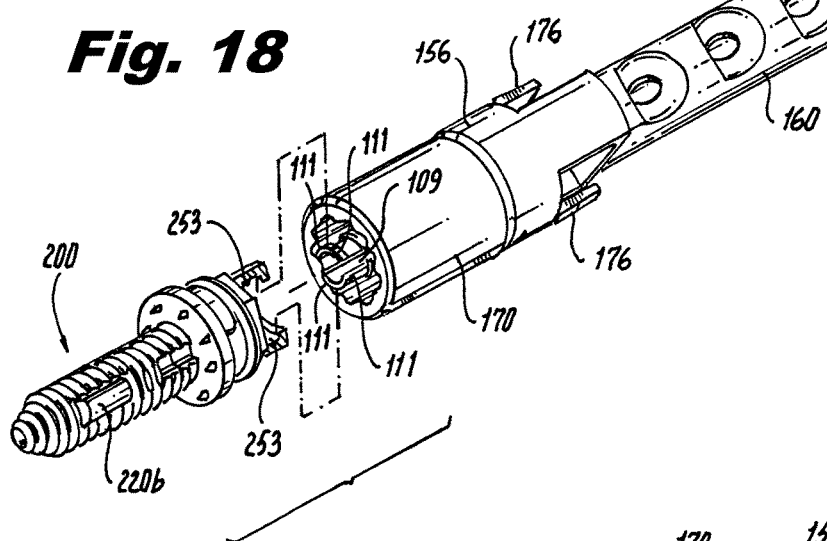
FIG. 18 is a perspective view of the adapter mounted on the spike cap drive of the instrument of FIG. 1 about to be coupled to the implant.

Referring now to FIG. 18, the matching adapter 170 is slid over the distal portion 108 of the main body 102 so that the legs 175, 176 can be inserted into the square opening 158. Preferably, the locking tabs 177 provide an audible click when the legs 176 deflect outward into the transverse locking passage 157 to confirm positive engagement for the user. The user can also visually confirm proper positioning of the adapter 170 because the alignment ridge 178 should align with the indicator arrow 123 on the socket end 156 as shown in FIG. 19.

Figure 19:
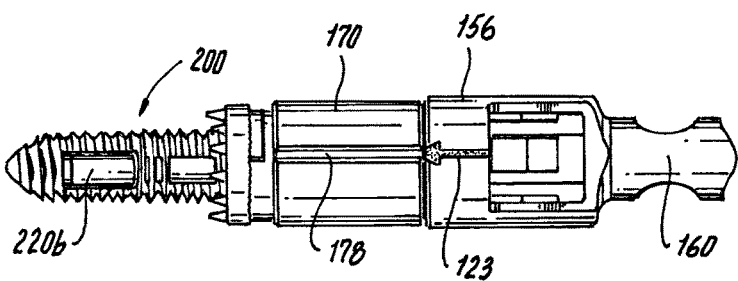
FIG. 19 is a side elevational view of the insertion instrument of FIG. 1 with the implant mounted thereon.

Referring to FIGS. 18 and 19, after positioning the adapter 170 on the drive shaft 160, the implant 200 can be partially engaged to the tip 113 by a snap friction fit. The tip 113 is slightly compressed, by virtue of the slots 109, and passed into the proximal internal recess 250 of the implant 200 with the blades 220a, 220b of the implant 200 aligned with the slots 109, arrow 123 and stripes 127 of the main body 102. As a result, the surgeon can determine proper blade orientation visually prior to and during insertion. The tip 113 stops within the recess 250 when the ridges 111 seat into the transverse groove 253. At this point, the implant 200 is coupled to the insertion instrument 100 but not yet "locked."

To lock the implant 200 to the instrument 100, the plunger 110 is moved from the unlocked position to the locked position. To move the plunger 110 distally, the plunger knob 126 is rotated clockwise (looking from the proximal end). As the threads are left-handed, the plunger 110 will move towards the distal tip 113. As the plunger 110 moves, the first distal axial groove portion 119 passes along the boss 139 of the plunger stop 132 until the boss 139 aligns with the radial portion 121 of the groove 116. When the boss 139 aligns with the radial portion 121 of the groove 116, the plunger stop 132 rotates clockwise because of the bias of the spring 141. The boss 139 passes into the radial portion 121 and further axial movement is prevented. The reference notch 131 of the wing 120 is at the locked indicia 105b and the insertion instrument is in the locked position.

In the locked position, the distal pushing end 112 of the plunger 110 is approximately flush with the distal tip 113 of the main body 102. Thus, the slots 109 of the main body 102 can no longer flex to allow the ridges 111 out of the transverse groove 253 best seen in FIG. 22. Consequently, the implant 200 is tightly coupled and locked to the tip 113 so that inadvertent removal does not occur. The insertion instrument 100 is now ready to have the socket end 156 of the spike cap drive 140 engaged to the hex nut 235 of the implant 200.

To engage the spike cap drive 140 to the hex nut 235 of the implant 200, the handle portion 148 is held to prevent rotation while the drive shaft 160 is rotated to bring the pins 165 out of the radial portion 164 of the slots 161. The spring 163 will bias the drive shaft 160 outward so care should be taken to slowly extend the drive shaft 160 to have the hex socket 172 properly engage the hex nut 235 of the implant 200 (best seen in FIG. 22). In order to have the hex socket 172 properly engage the hex nut 235, a slight manual rotation or jiggle of the drive shaft 160 may be required. The implant 200 is now locked to the insertion instrument 100 to be ready for spinal implantation. The force provided by the spring 163 is optimized to insure proper, reliable engagement between the adapter 170 and hex nut 235 while providing excessive force to interfere with the operation of the insertion instrument 100 or deployment of the implant 200.

Deploying the Implant in the Interspinous Space

Figure 20:
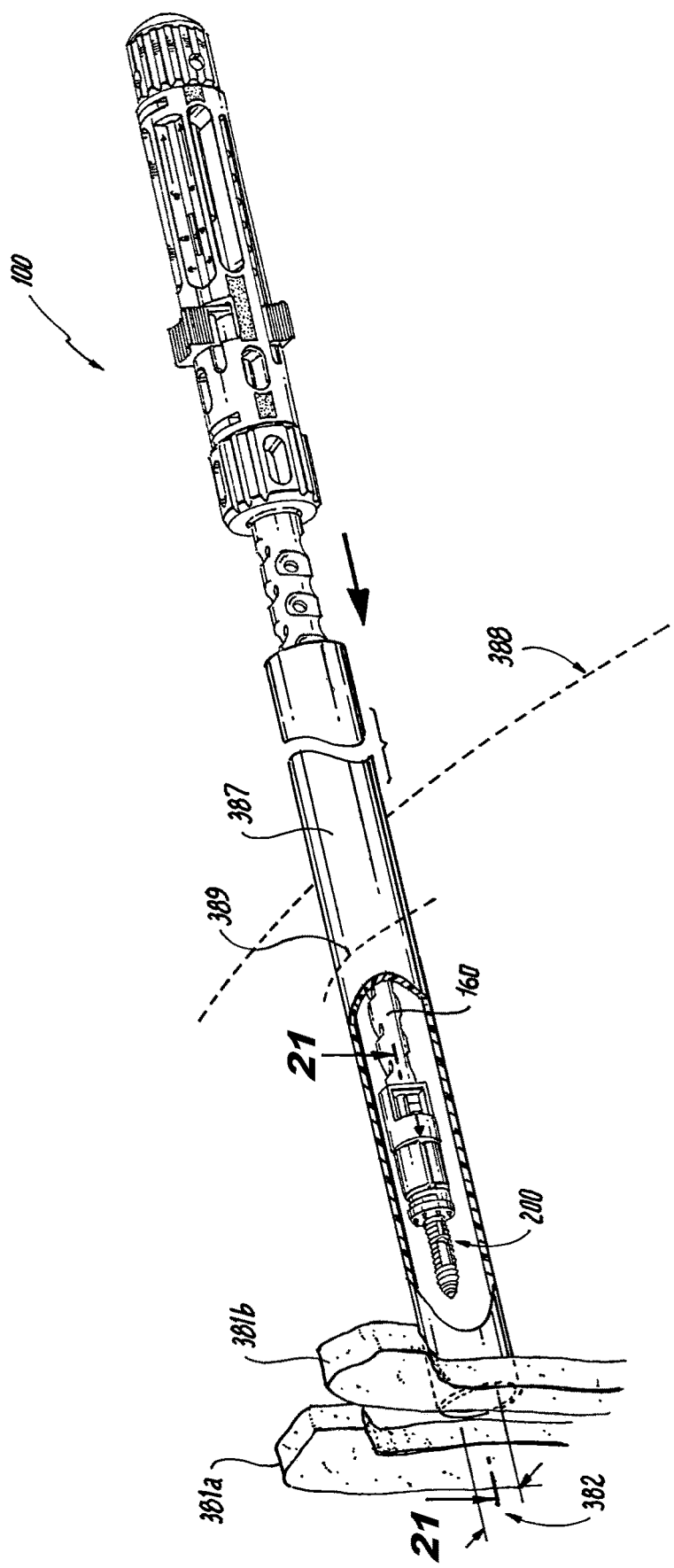
FIG. 20 is a perspective view, illustrating an implant in preparation to be installed dorsally.
Figure 21:
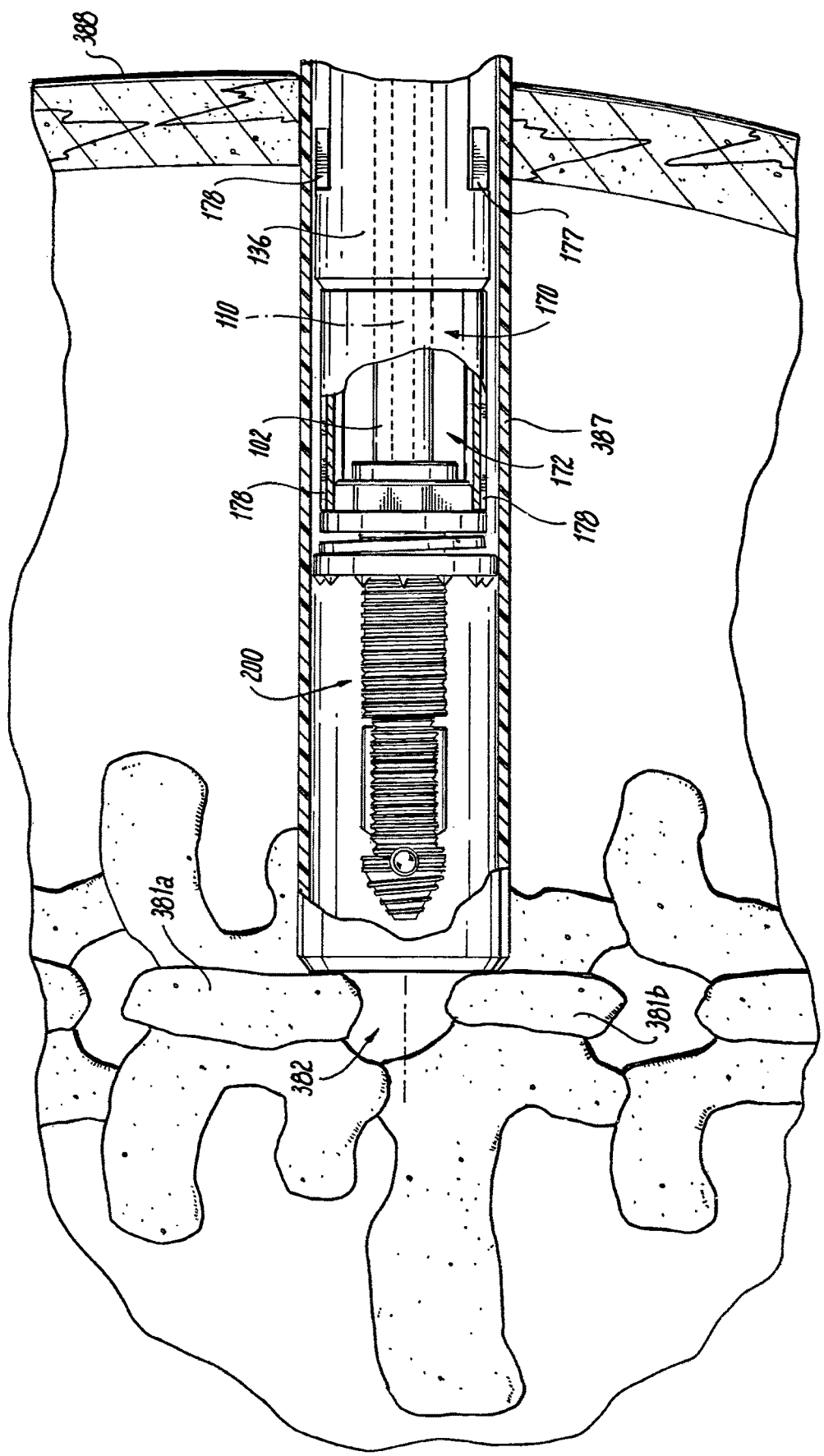
FIG. 21 is a dorsal view of an implant within an introducer tube during lateral insertion thereof.

FIGS. 20-24 illustrate various stages during insertion and placement of the implant 200 into a target interspinous process space 382. In short, FIG. 20 is a perspective view of the implant 200 locked to the insertion instrument 100, in preparation to be installed dorsally through a curved introducer tube 387, which has been inserted through an incision 389 formed through the skin 388 of a patient. FIG. 21 is a dorsal (rear) view of the implant 200, still held by the elongated insertion instrument 100, within a lumen of an introducer tube 387, during lateral insertion thereof.

Figure 22:
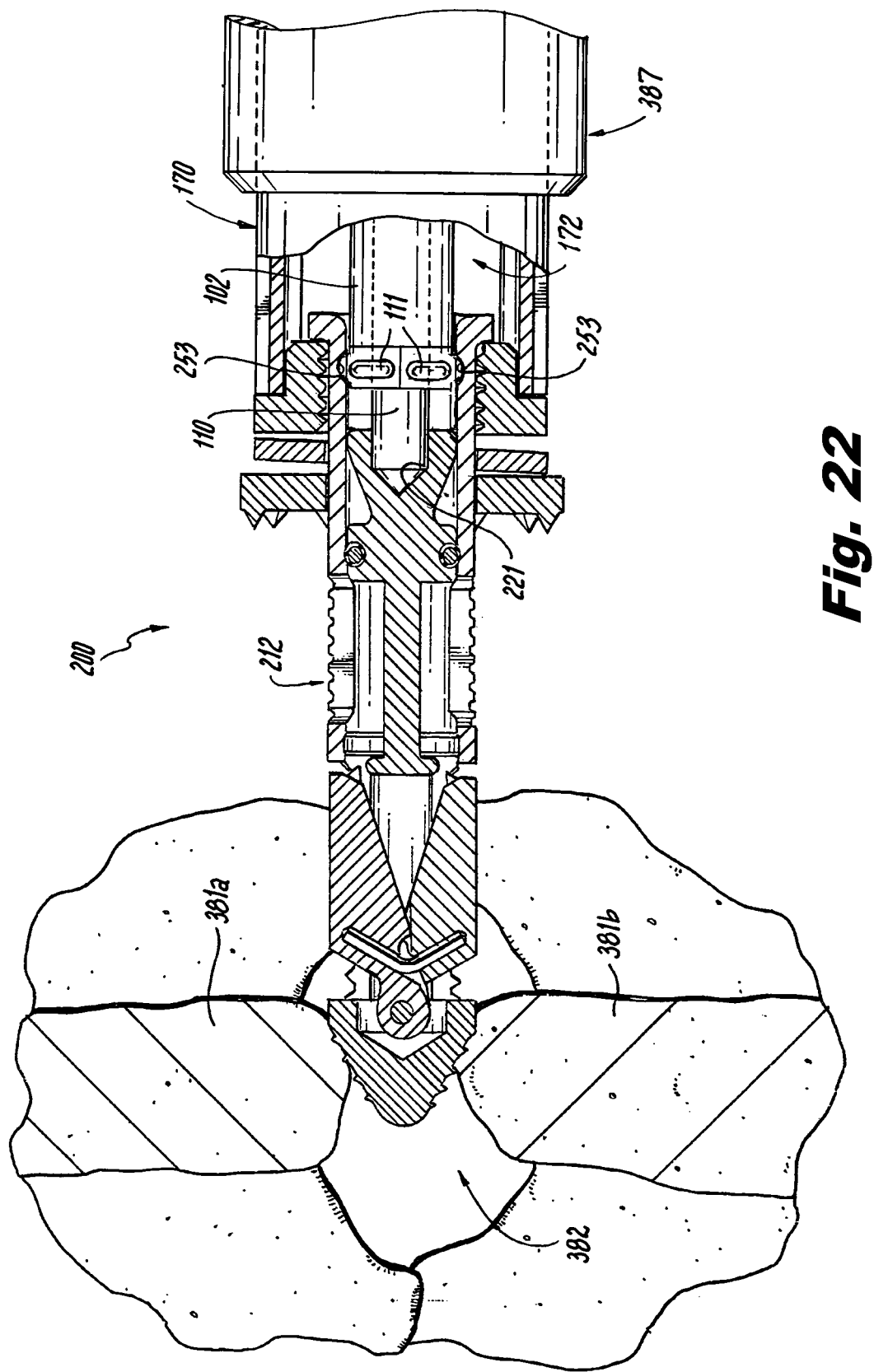
FIG. 22 is a dorsal view illustrating the implant being screwed into a target interspinous process space.
Figure 27:
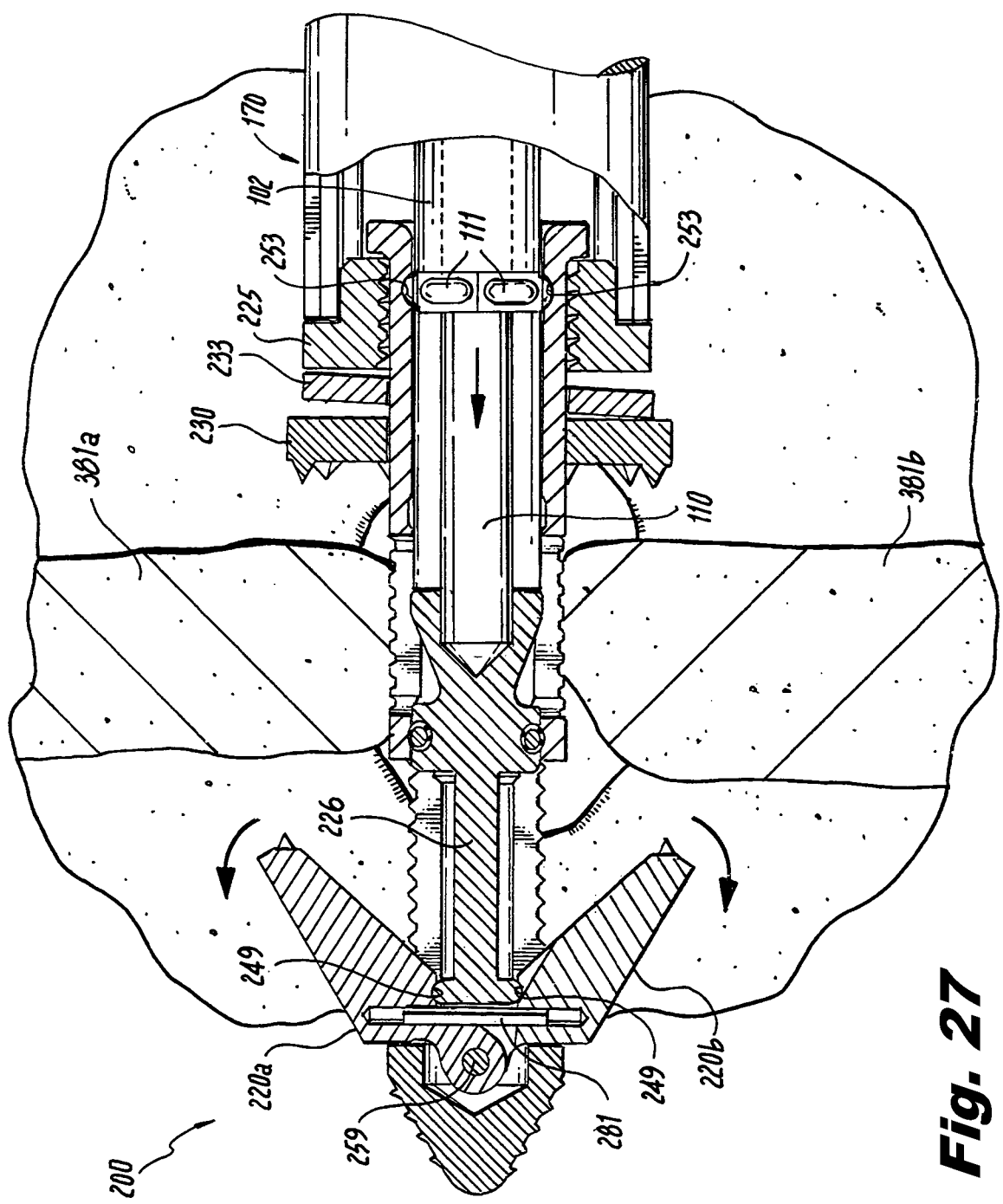
FIG. 27 is cross-sectional view illustrating the deployment of the blades of the implant.
Figure 28:
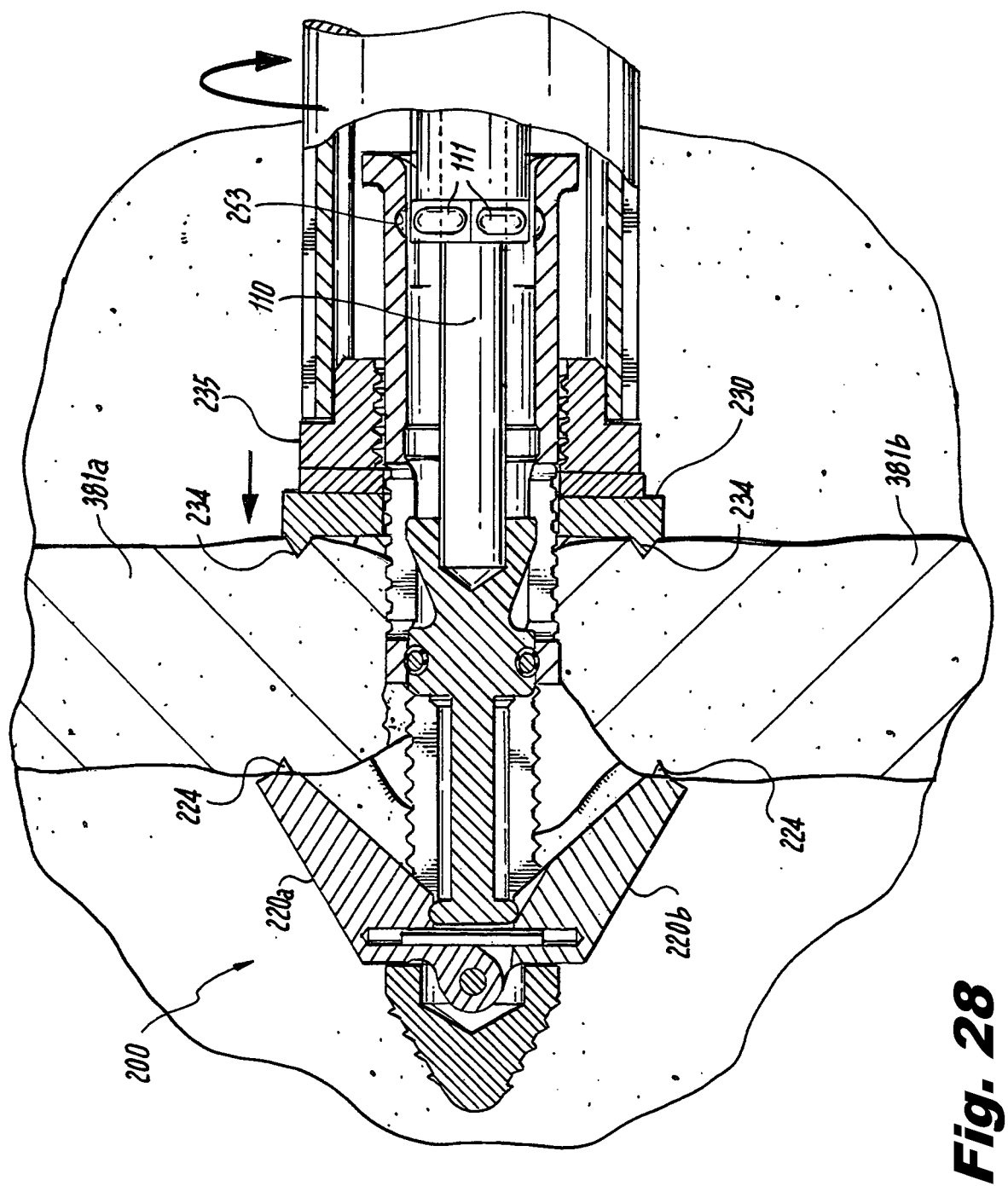
FIG. 28 is a cross-sectional view illustrating the spike cap drive securing the implant to the spinous processes.
Figure 30:
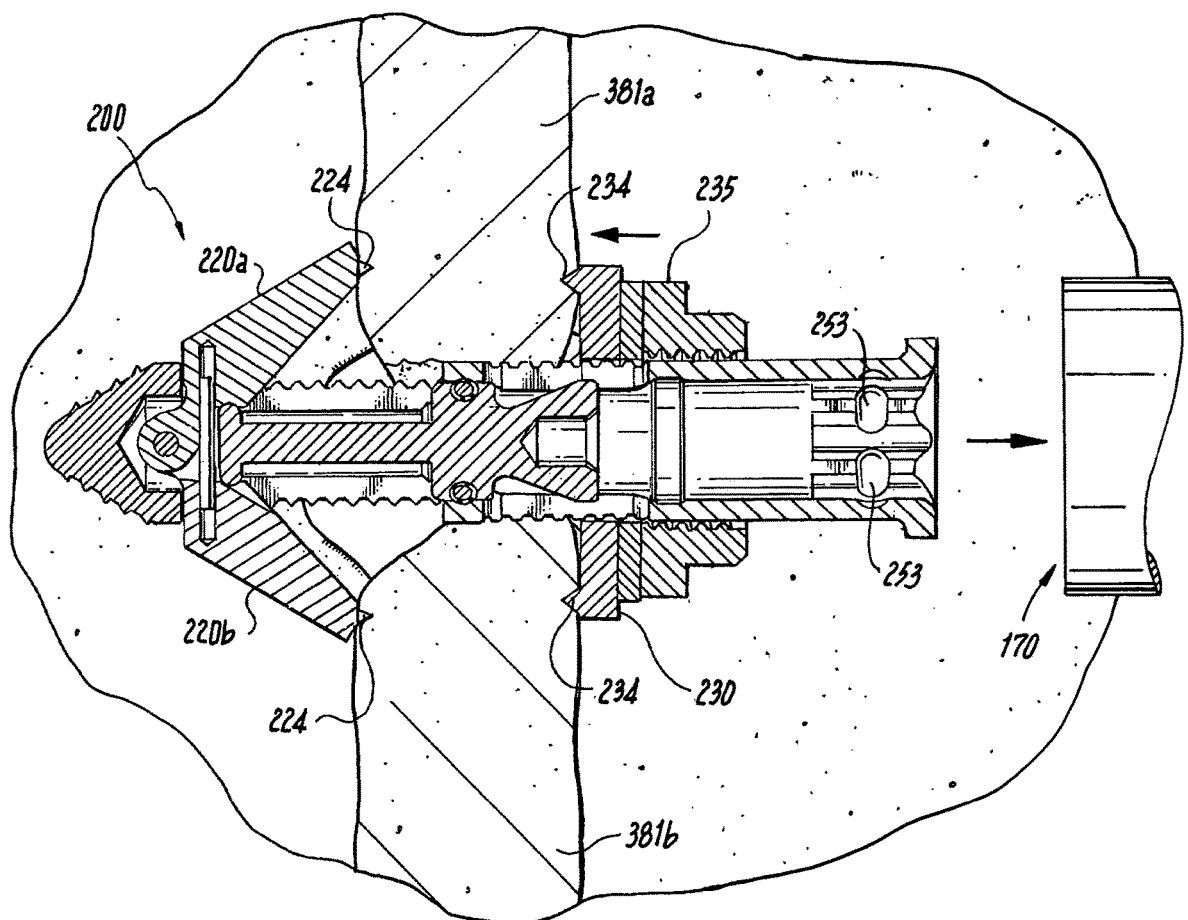
FIG. 30 is a dorsal cross-sectional view of the implant fixed in the spinal column with the insertion instrument removed.

FIG. 22 is a dorsal view illustrating the implant 200 being laterally advanced to the target interspinous process space 382, under application of a rotational force applied by the insertion instrument 100, by virtue of the threads 222 provided on the body 212 thereof. FIG. 27 is a dorsal view illustrating the implant 200 with the internal implant plunger 226 urged distally, effecting deployment of the distal anchor elements—in this case, blades 220a, 220b. The nut 235 is then tightened, which urges the body 212 proximally, and thus also urges the blades 220 more securely against the adjacent bony structure, impinging the spinous processes 381a, 381b there between, as shown in FIG. 28, which is a dorsal view illustrating the implant 200 with the spike cap 230 urged distally by the nut 235, engaging the adjacent spinous processes 381a, 381b. FIG. 30 is a dorsal view illustrating the implant 200 fixed in place with removal of the insertion instrument 100.

More particularly, as seen in FIG. 20, a sleeve 387 is provided to facilitate insertion. The insertion methods can include use of a stylet, dilators, and the like to gain access and define a path for the sleeve 387, as will be described in more detail below. However, dorsal insertion can be accomplished as set forth in U.S. patent application Ser. No. 12/011,905, filed Jan. 30, 2008 (U.S. Pub. No. 2009/0054988), which is incorporated herein by reference in its entirety.

As illustrated, in FIG. 20, dorsal insertion of the subject implants, represented by implant 200, can be effected by forming an incision 389 through the skin 388 of a patient, at a level corresponding to a target interspinous process space 382, defined between adjacent vertebral processes 381a, 381b. With dorsal entry illustrated in FIG. 20, the path traversed by the implant 200, and therefore also by the sleeve 387 is curved to align the path and the implant 200 with the target interspinous process space 382. As such, the insertion instrument 100 may be flexible and/or curved to match the curve of the sleeve 387.

FIG. 21, in contrast, illustrates direct lateral insertion of the implant 200 into the target interspinous process space 382. In this arrangement, an incision is formed in the skin 388 of a patient, and ultimately a sleeve 387 is advanced through the tissue to the target interspinous process space 382, through which the implant 200 is advanced, connected to the insertion instrument 100. As shown in FIGS. 21 and 22, of which FIG. 22 is illustrated for clarity without the sleeve 387, the implant 200 is axially rotated by way of the insertion instrument 100, thus threading the implant 200 into the target interspinous process space 382, distracting the adjacent spinous processes 381a, 381b, and advancing the implant 200, generally centered with respect to the spinous processes 381a, 381b.

To rotate the implant 200, the proximal handle portion 103 of the main body 102 is rotated in a tightening or clockwise direction to self-thread the implant 200 through the interspinous space 382 as shown in FIG. 22. During the rotation of the implant 200, the implant 200 distracts the interspinous space. Relative rotation and axial translation between the implant 200 and the insertion instrument 100 is inhibited because the implant 200 is locked onto the tip 113 by the distal pushing end 112 of the plunger 110. Distraction can also be performed in advance by a separate instrument, with insertion of the implant 200 following, and maintaining such distraction.

Figure 24:
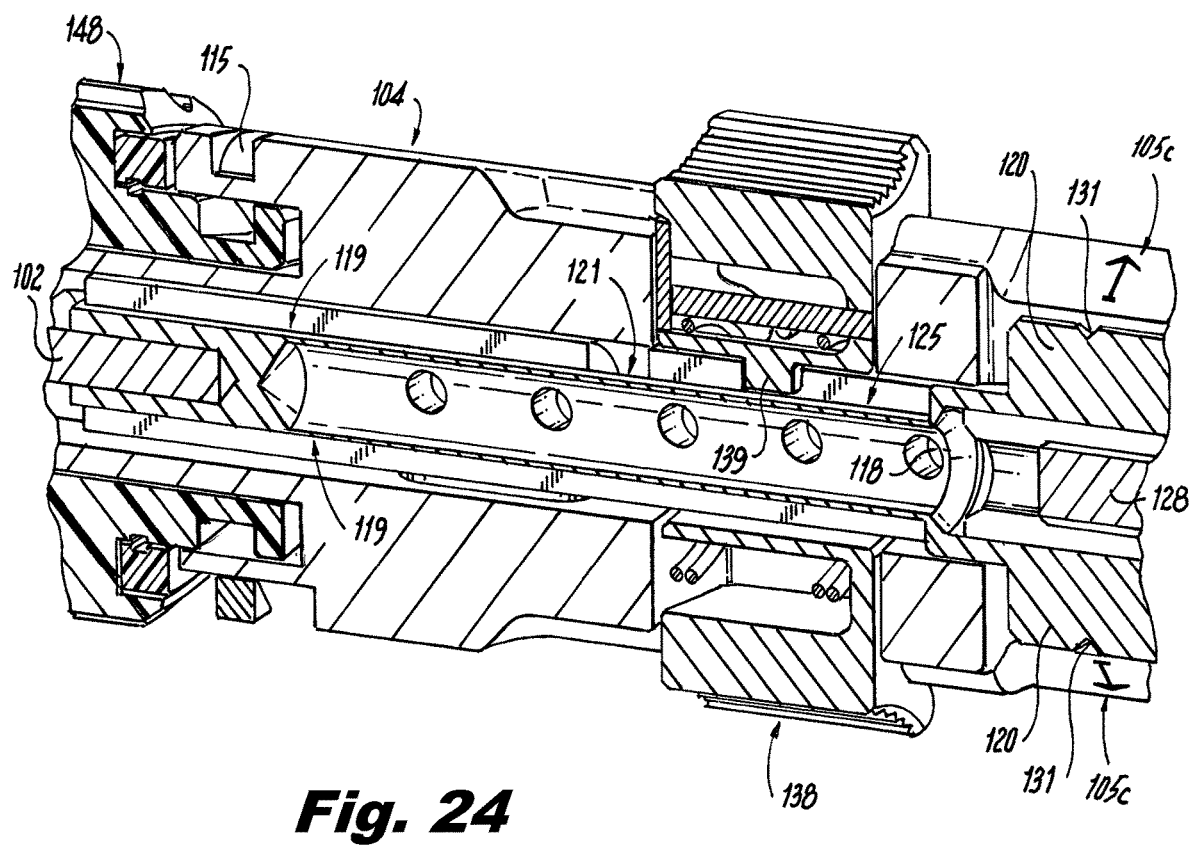
FIG. 24 is a cross-sectional view of the insertion instrument showing the plunger and plunger stop as the implant blades are being deployed.
Figure 25:
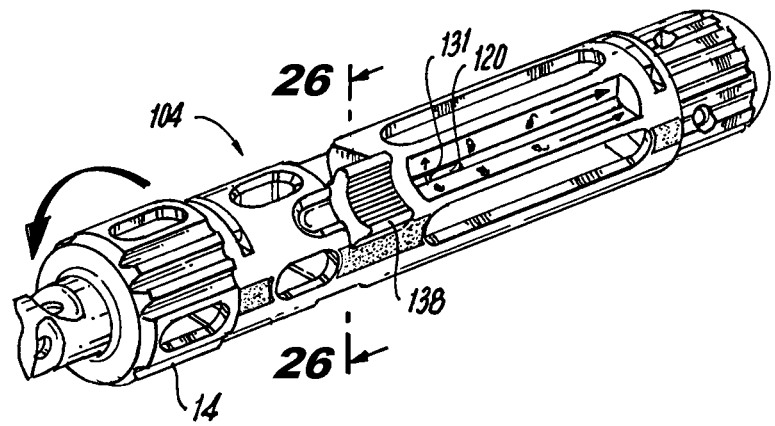
FIG. 25 is a perspective view of the insertion instrument illustrating the spike cap drive being utilized to turn the hex nut of the implant.
Figure 26:
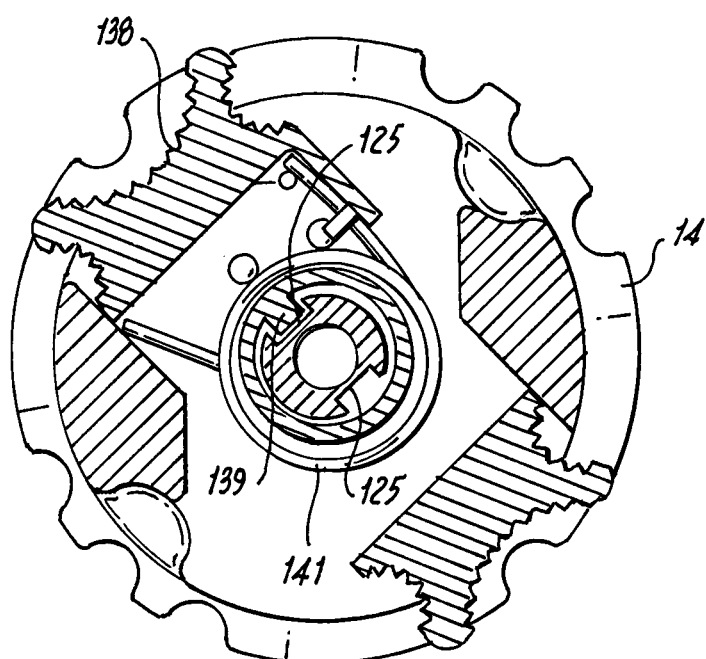
FIG. 26 is a cross-sectional view of the insertion instrument showing the plunger and plunger stop in the locked position.

When anchoring blades 220a, 220b have passed through the interspinous space 382 as shown in FIG. 27, the anchoring blades 220a, 220b can be deployed. Referring now to FIGS. 23 and 24, to deploy the anchoring blades 220a, 220b, the plunger stop 132 is rotated so that the boss 139 moves out of the radial groove portion 121 of the plunger 110. As such, the plunger 110 becomes free to move with the axial portion 125 sliding along the boss 139 of the plunger stop 132 as shown best in FIG. 24. To accomplish the proximal movement of the plunger 110, the plunger stop 132 is held and the plunger knob 126 is turned clockwise or in a tightening motion. Because the threading is left-handed, the plunger 110 will move away from the plunger knob 126. The reference notch 131 will slide toward the "deployed" position indicia 105c as the second proximal axial groove portion 125 rides along the boss 139.

As the plunger 110 extends distally, the distal pushing end 112 seats in the recess 221 of the implant plunger 226. As the plunger 110 continues to move distally, the pushing end 112 applies pressure and moves the implant plunger 226 distally to deploy the blades 220a, 220b as shown in FIG. 27. Once fully deployed, the reference notch 131 will be adjacent the "deployed" indicia 105c and turning of the plunger knob 126 can stop. The physician can also verify proper deployment of the blades 220a, 220b by fluoroscopy. Once the blades 220a, 220b are deployed, the implant 200 can be set in final position.

Referring now to FIG. 28, the hex nut 235 of the implant 200 is shown being driven by the spike cap drive 140 to engage the spikes 224, 234 to the spinous processes 381a, 381b. The spike cap drive 140 rotates the hex nut 235 to move the spike cap 230 distally. Because the spike cap 230 is keyed to the implant 200 to prevent rotation, as the hex nut 235 turns, the spike cap 230 slides distally.

To rotationally drive the hex nut 235, the spike cap drive 140 is rotated clockwise relative to the main body 102 by the handle portion 148. Turning the handle portion 148 turns the adapter 170 and thereby the hex nut 235. Once the spike cap 230 engages the spinous processes 381a, 381b, the blades 220a, 220b are drawn proximally into engagement with the bone 381a, 381b. A flat portion of the implant 200 is not threaded so that the implant 200 slides proximally. While the spike cap drive 140 is used to tighten the hex nut 235, the surgeon can feel the spike cap 230 become fully seated or full seating is seen in an accompanying fluoroscopy display. Preferably, one or more osteogenesis promoting substances can be packed in and/or around the implant 200 to promote bone ingrowth and/or spinal fusion, if desired.

A separate tap can be used in the target interspinous process space 382 before the insertion of the implant 200, or as mentioned above, the implant 200 can be provided with features that provide self-tapping capability. Methods of lateral insertion of the spinal implant 200 into a target interspinous process space 382 can include, following forming the incision, inserting a stylet (not illustrated) through the incision 389, laterally to the target interspinous process space 382, preferably using an internal imaging technique, such as fluoroscopy.

Figure 29:
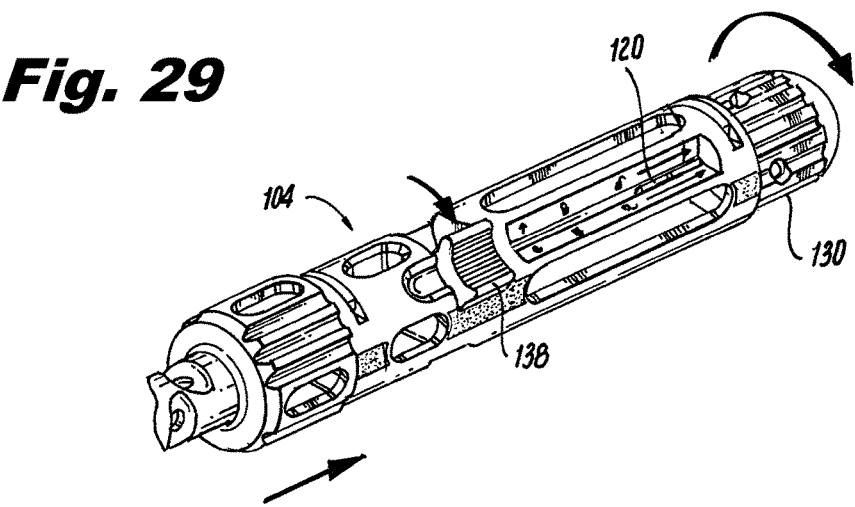
FIG. 29 is a perspective view of the insertion instrument with the plunger being retracted from the implant in preparation to remove the insertion instrument from the implant after deployment of the implant in the spinal column.

Referring now to FIGS. 29 and 30, once the implant 200 is properly deployed, the insertion instrument 100 is disengaged from the implant 200. To disengage the insertion instrument 100, the drive shaft 160 of the spike cap drive 140 is retracted into the intermediate portion 154 with the pins 165 captured in the radial portion 164 of the slot 161 following the same procedure as described above so that the adapter 170 disengages from the hex nut 235. The plunger stop 132 is rotated and held by the user's thumb so that the groove 116 will ride from the proximal axial portion 125 to the distal axial portion 119 without passing into the radial portion 121. To withdraw the plunger 110, the plunger knob 126 is loosened or rotated in the counter-clockwise direction relative to the handle portion 104 of the main body 102 until the reference notch 131 fully indicates the "unlocked" position next to the unlocked indicia 105a. As the plunger 110 withdraws from the tip 113, the slots 109 are again allowed to flex so that the tip 113 pops out of the proximal internal recess 250 of the implant 200. With the adapter 170 disengaged and the plunger 110 retracted to the unlocked position, the coupling force of the tip 113 to the implant 200 can be overcome to fully detach the insertion instrument 100. Once removed, the insertion instrument 100 can be removed from the patient for disassembly, cleaning and re-use.

Referring now to FIGS. 29 and 30, once the implant 200 is properly deployed, the insertion instrument 100 is disengaged from the implant 200. To disengage the insertion instrument 100, the plunger knob 126 is loosened or rotated in the counter-clockwise direction relative to the handle portion 104 of the main body 109 to withdraw the plunger 110 until the reference notch 131 fully indicates the "locked" position next to the unlocked indicia 105b. The plunger stop 132 clicks over, bringing the boss 139 into the radial groove portion 121, and engages to prevent further loosening of the plunger 110. The plunger stop 132 is rotated and held by the user's thumb so that the groove 116 will ride from the radial groove portion 121 to the distal axial portion 119. This retraction of the plunger 110 may also be accomplished without the boss 139 passing into the radial groove portion 121. As the plunger 110 withdraws from the tip 113 by further counter-clockwise rotation of the plunger knob 126, the slots 109 are again allowed to flex so that the tip 113 can pop out of the proximal internal recess 250 of the implant 200. With the adapter 170 disengaged and the plunger 110 retracted to the unlocked position, the coupling force of the tip 113 to the implant 200 can be overcome to fully detach the insertion instrument 100. Once removed, the insertion instrument 100 can be removed from the patient for disassembly, cleaning and re-use.

Disassembly of the Insertion Instrument

It is advantageous to disassemble the insertion instrument 100 for cleaning. Referring to FIGS. 3-10 in reverse, the locking tabs 117 that retain the plunger 110 are flipped up to unlock the plunger 110. As long as the plunger 110 is in the unlocked position, the plunger 110 can then be removed from the main body 102. The plunger knob 126 can be unscrewed from the plunger 110. Once the plunger 110 is removed, the plunger stop 132 can also be removed from the main body 102. Next, the locking tabs 115 that retain the spike cap drive 140 are released so that the spike cap drive 140 can be removed from the main body 102. The adapter 170 can be unsnapped from the spike cap drive 140. At this point, the components of the insertion instrument 100 are ready to be cleaned.

Alternative Embodiment

Figure 31:
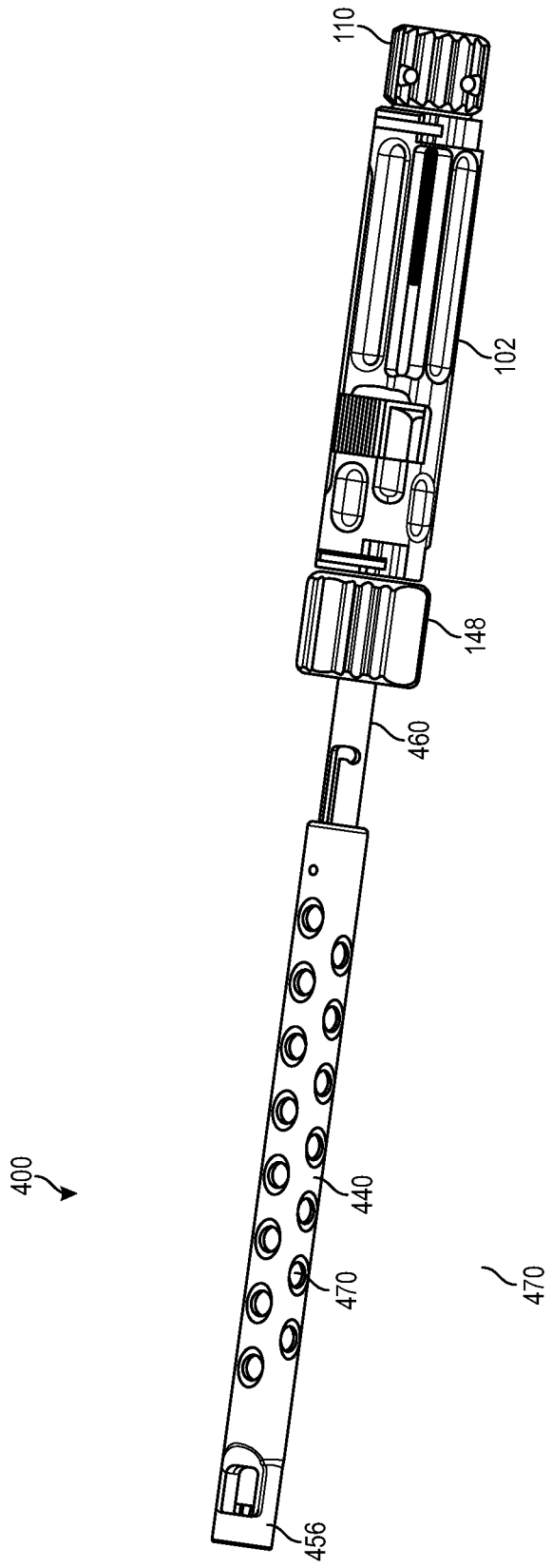
FIG. 31 is a perspective view of an embodiment of the insertion instrument.

Illustrated in FIGS. 31-34 is an embodiment of an insertion instrument 400. With reference to FIG. 31, similar to aforementioned embodiments, insertion instrument 400 comprises the elongated main body 102, plunger 110, and the handle portion 148, as well as other components described above. In some embodiments of insertion instrument 400, the handle portion 148 operatively engages a proximal drive shaft 460 rather than a spike cap drive 140, as described previously.

In some embodiments, the insertion instrument 400 includes the proximal drive shaft 460 located proximally of distal spike cap drive 440. The distal spike cap drive 440 defines an axial passage 444 extending therethrough. The distal spike cap drive 440 terminates in a socket end 456. The socket end 456 is tubular but forms a shaped opening 458, which may be square, for coupling, either directly or indirectly, to the implant 200. The socket end 456 also forms a transverse locking passage 457, which may be square. Distal spike cap drive 440 may also include openings 470 within the walls to reduce the weight of the element or to assist with cleaning of the instrument.

The axial passage 444 of the distal spike cap drive 440 is configured to receive the distal section of the proximal drive shaft 460. For example, with reference to FIG. 31-34, the elongated main body 102 may be received within the proximal drive shaft 460 and the distal end and tip 113 of the main body 102 may extend distally therefrom. Distal to the proximal drive shaft 460, a spring 463 may surround a portion of the elongated main body 102 that extends distally from the proximal drive shaft 460. Subsequently, in some embodiments, the axial passage 444 of the distal spike cap drive 440 may receive the spring 463, a portion of the elongated main body 102, and a distal portion of the proximal drive shaft 460.

In some embodiments, the distal spike cap drive 440 is secured to and operatively engages the proximal drive shaft 460. This may be accomplished by fastening pins 465 through one or more pin holes 467. As can be seen from FIG. 32, the pins 465 may be configured to insert into complementary slots 461 in proximal drive shaft 460 when insertion instrument 400 is assembled.

Figure 32:
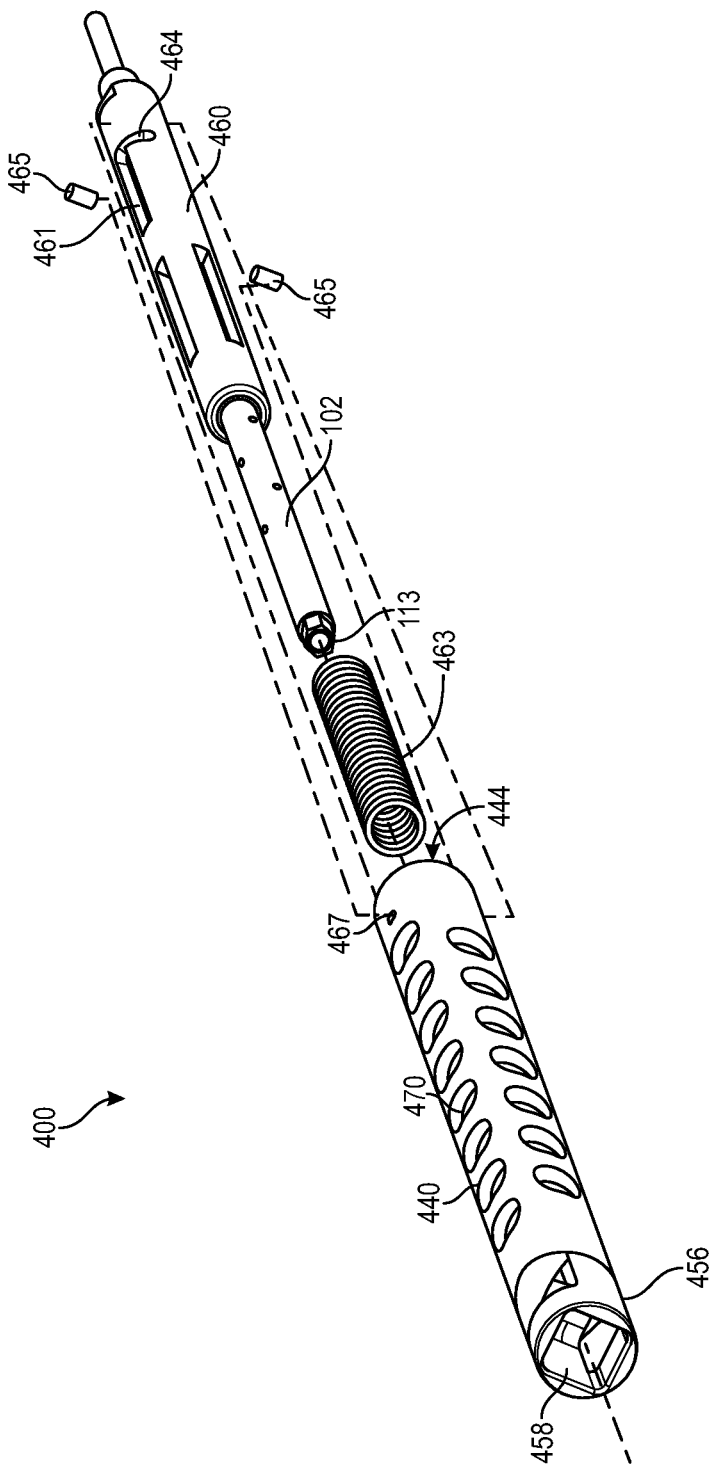
FIG. 32 is an exploded view of components of the insertion instrument of FIG. 31, in some embodiments.

Additionally, when fully assembled, the tip 113 of elongated main body 102 may extend into the socket end 456, terminating near opening 458 (see FIG. 32). Similar to the description above, tip 113 may be configured to operatively engage an implant 200. As will be described below, displacement of the distal spike cap drive 440 may reveal tip 113, such that a user may secure the implant 200 to tip 113.

Figure 33:
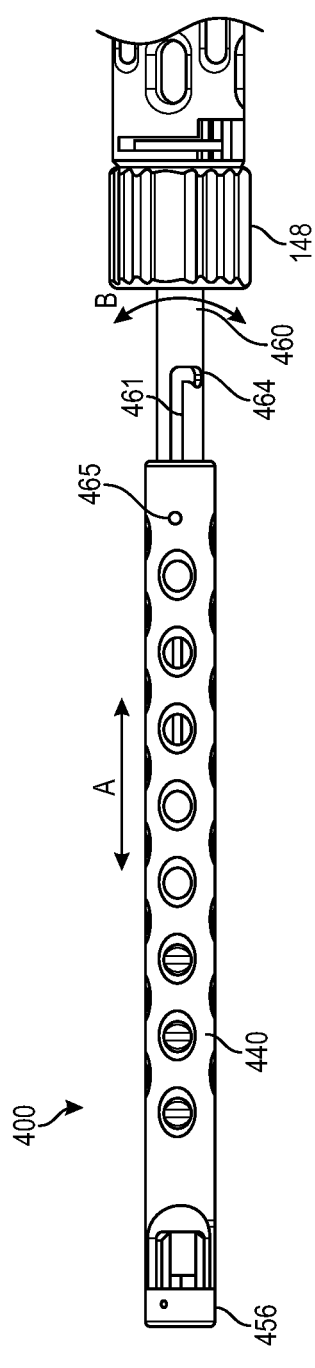
FIG. 33 is a side view of some embodiments of the insertion instrument of FIG. 31 in an extended configuration.
Figure 34:
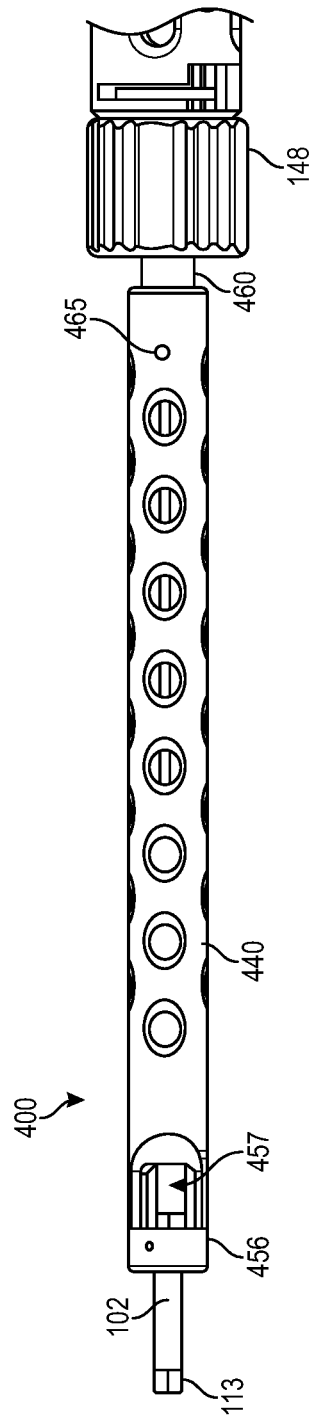
FIG. 34 is a side view of some embodiments of the insertion instrument of FIG. 31 in a retracted configuration.

Referring now to FIGS. 33 and 34, operation of the distal spike cap drive 440 and proximal drive shaft 460 is discussed. As mentioned above, the positioning of the distal spike cap drive 440 in relation to the proximal drive shaft 460 may allow for the tip 113 of the elongated main body 102 to be accessible. For example, when fully assembled, the pins 465 may be received by complementary slots 461. As depicted in FIG. 33, this may allow for movement of distal spike cap drive 440 along a longitudinal direction (e.g., direction A). It will be noted that in some embodiments, spring 463 biases the distal spike cap drive 440 in the distal direction in comparison to the proximal drive shaft 460 (i.e., away from proximal drive shaft 460). Therefore, to adjust distal spike cap drive 440 along direction A in the proximal direction, a user must overcome the force of spring 463.

In some embodiments, complementary slots 461 disposed on proximal drive shaft 460 may comprise a radial portion 464. Accordingly, once distal spike cap drive 440 is moved substantially along direction A, the pins 465 may abut radial portion 464, thus preventing further movement along direction A. Once stopped, a user may twist distal spike cap drive 440 along direction B, such that pins 465 travel along and inside radial portion 464. As shown in FIG. 34, such a movement of the distal spike cap drive 440 may distally extend the tip 113 of the main elongated body 102. Additionally, by placing pins 465 in the radial portion 464, the distal spike cap drive 440 is secured in the retracted position. Such a motion is similar to that described above with reference to FIG. 17, however in these embodiments it is the distal spike cap drive 440 that is adjustable along direction A and direction B, rather the drive shaft 160 as described in some embodiments.

By placing the distal spike cap drive 440 in the secured position, as shown in FIG. 34, a user may place an adapter (e.g., adapter 170) over the distal portion 108 of the elongated main body 102 so that the legs 175, 176 can be inserted into the opening 458. In some embodiments, the locking tabs 177 provide an audible click when the legs 176 deflect outward into a transverse locking passage 457 to confirm positive engagement for the user. In some embodiments, the user may visually confirm proper positioning of the adapter 170 because the alignment ridge 178 aligns with the indicator arrow 123 on the socket end 456.

After positioning the adapter 170 on the distal spike cap drive 440, the implant 200 may be partially engaged to the tip 113 by a snap friction fit. In some embodiments, the tip 113 is slightly compressed, by virtue of the slots 109, and passed into the proximal internal recess 250 of the implant 200 with the blades 220a, 220b of the implant 200 aligned with the slots 109, arrow 123, and stripes 127 of the elongated main body 102. As a result, the user can determine proper blade orientation visually prior to and during insertion. The tip 113 stops within the proximal internal recess 250 when the ridges 111 seat into the transverse groove 253. At this point, the implant is coupled to the insertion instrument 400 but not yet "locked."

In some embodiments, to lock the implant 200 to the insertion instrument 400, the plunger 110 is moved from the unlocked position to the locked position. To move the plunger 110 distally, the plunger knob 126 is rotated clockwise (looking from the proximal end). As the threads are left-handed, the plunger 110 will move towards the tip 113. As the plunger 110 moves, the first distal axial groove portion 119 passes along the boss 139 of the plunger stop 132 until the boss 139 aligns with the radial portion 121 of the groove 116. When the boss 139 aligns with the radial portion 121 of the groove 116, the plunger stop 132 rotates clockwise because of the bias of the spring 141. The boss 139 passes into the radial portion 121 and further axial movement is prevented. The reference notch 131 of the wing 120 is at the locked indicia 105*b* and insertion instrument 400 is in the locked position.

In some embodiments, in the locked position, the distal pushing end 112 of the plunger 110 is approximately flush with the tip 113 of the elongated main body 102. Thus, the slots 109 of the elongated main body 102 can no longer flex to allow the ridges 111 out of the transverse groove 253 as best seen in FIG. 22. Consequently, the implant 200 is tightly coupled and locked to the tip 113 so that inadvertent removal does not occur. The insertion instrument 400 is now ready to have the socket end 456 of the distal spike cap drive 440 engaged to the adapter 170, which in turn may engage the hex nut 235 of the implant 200.

In some embodiments, to engage the distal spike cap drive 440 to the hex nut 235 of the implant 200, the handle portion 148 is held to prevent rotation while the distal spike cap drive 440 is rotated to bring the pins 465 out of the radial portion 464 of the complementary slots 461. The spring 463 will bias the distal spike cap drive 440 distally so care should be taken to slowly extend the distal spike cap drive 440 to have the hex socket 172 of adapter 170 properly engage the hex nut 235, a slight manual rotation or jiggle of the distal spike cap drive 440 may be required. In some embodiments, the implant 200 is now locked to the insertion instrument 400 and may be ready for spinal implantation. The force provided by the spring 463 is optimized to ensure proper, reliable engagement between the adapter 170 and hex nut 235, while not providing excessive force to interfere with the operation of the insertion instrument 400 or deployment of the implant 200.

The particular arrangement of components of insertion instrument 400 may provide certain advantages to a user while operating the device. For example, in the configuration of FIGS. 31-34, a user may be able to access the proximal drive shaft 460 while the insertion instrument 400 is in use from outside the body. As described earlier with reference to FIG. 20, when operating insertion instrument 400 inside of the introducer tube 387, the user has access to the proximal drive shaft 460 and distal spike cap drive 440. This allows the user to adjust the distal spike cap drive 440 in relation to the proximal drive shaft 460 while functioning. For instance, the user may adjust the positioning of pins 465 along complementary slots 461 or radial portion 464 during use.

In one example, during an operation, the tissue of a patient may displace the adapter 170 from the hex nut 235. In such a case, having the distal spike cap drive 440 accessible to the user may allow the user to manipulate the distal spike cap drive 440 to re-engage the adapter 170 and the hex nut 235. In another example, if a user forgets to engage the distal spike cap drive 440 with the hex nut 235 before insertion into the patient, they can still correct this during the procedure. In this example, if the implant 200 is partially threaded into tissue of a patient while operatively connected to the insertion instrument 400, the user may access the distal spike cap drive 440 during operation to engage the hex nut 235. Such access allows the user to maintain the coupling of the insert 200 to the insertion instrument 400 throughout the operation. This avoids the user from having to withdraw the entire inserter and implant and restart the procedure entirely.

Below is Table 1, which is a parts list for the insertion instrument 100 and implant 200 illustrated in the figures.

TABLE 1

| Part | Ref. No. |
| --- | --- |
| insertion instrument | 100 |
| elongated main body | 102 |
| axial wing slot | 103 |
| proximal handle portion | 104 |
| "unlocked" position indicia | 105a |
| "locked" position indicia | 105b |
| "deployed" position indicia | 105c |
| central passage | 106 |
| distal portion | 108 |
| axial slots | 109 |
| plunger | 110 |
| outer ridges | 111 |
| distal pushing end | 112 |
| tip | 113 |
| locking end | 114 |
| locking tabs | 115 |
| groove | 116 |
| second pair of opposing locking tabs | 117 |
| radial holes | 118 |
| first distal axial groove portion | 119 |
| opposing radial wings | 120 |
| radial groove portion | 121 |
| proximal recess | 122 |
| indicator arrow | 123 |
| axial threaded post | 124 |
| second proximal axial groove portion | 125 |
| plunger knob | 126 |
| stripes | 127 |
| threaded distal end | 128 |
| proximal handle portion | 130 |
| reference notch | 131 |
| plunger stop | 132 |
| distal guide portion | 133 |
| axial recess | 134 |
| angled surface | 135 |
| axial passage | 136 |
| tubular portion | 137 |
| outer opposing lands/thumb lands | 138 |
| boss | 139 |
| spike cap drive | 140 |
| biasing spring | 141 |
| annular recess | 142 |
| ends | 143 |
| axial passage | 144 |
| proximal portion | 146 |
| handle portion | 148 |
| interlocking portion | 150 |
| annular groove | 152 |
| intermediate portion | 154 |
| socket end | 156 |
| transverse square locking passage | 157 |
| square opening | 158 |
| drive shaft | 160 |
| complementary slots | 161 |
| spring | 163 |
| radial portion | 164 |
| pins | 165 |
| pin holes | 167 |
| adapter | 170 |
| hex socket | 172 |
| central axial passage | 173 |
| standard male square open proximal end | 174 |
| rigid legs | 175 |
| flexible legs | 176 |
| locking tab | 177 |
| outer axial alignment ridges | 178 |

TABLE 1-continued

| Part | Ref. No. |
|---|---|
| implant | 200 |
| body | 212 |
| expanded-diameter portion | 213 |
| apertures | 214 |
| flat portions | 217 |
| distal blades | 220 |
| proximal internal recess | 221 |
| threads | 222 |
| hinge portions | 223a, 223b |
| spikes | 224 |
| proximal head | 225 |
| actuation plunger | 226 |
| catch | 227 |
| head portion | 228 |
| recess | 229 |
| spike cap | 230 |
| lock washer | 233 |
| hex nut | 235 |
| guide correspondingly shaped portions | 237 |
| inner cam surfaces | 240 |
| detent | 249 |
| bore | 250 |
| shaped socket | 251 |
| transverse grooves | 253 |
| annular grooves/recesses | 254 |
| pin | 259 |
| spring element | 281 |
| spinous processes | 381a, 381b |
| interspinous process space | 382 |
| introducer tube | 387 |
| skin | 388 |
| incision | 389 |
| insertion device | 392 |
| insertion instrument | 400 |
| distal spike cap drive | 440 |
| axial passage | 444 |
| socket end | 456 |
| transverse locking passage | 457 |
| opening | 458 |
| proximal drive shaft | 460 |
| complementary slots | 461 |
| spring | 463 |
| radial portion | 464 |
| pins | 465 |
| pin holes | 467 |
| openings | 470 |

Many of the primary structural components of the implant devices described herein are preferably formed from biological and/or biocompatible materials, including metal, ceramic, polymeric and/or composite materials that can be selected to have a modulus of elasticity that is substantially similar to that of bone, for example, polyetheretherketone thermoplastic (PEEK), machined bone, a titanium alloy or stainless steel, for example. The insertion instrument can additionally take advantage of polytetrafluoroethylene (PTFE) plastic with low coefficients of friction, abrasion resistance, a wide range of operating temperatures, and chemical inertness to form bearing surfaces on the rotating components to prevent metal wear and galling. PTFE is particularly useful for the portions of adjacent components that rotate with respect to each other.

While the apparatuses and methods of subject invention have been shown and described with reference to preferred embodiments, it is to be understood that any feature described in connection with one embodiment can be advantageously applied to other embodiments of the invention, even if not explicitly described in connection therewith, if such feature(s) are not mutually exclusive with other features of such embodiment. Nevertheless, those skilled in the art will readily appreciate that further changes or modifications may be made to devices and methods of the present invention without departing from the spirit and scope thereof. It is also to be appreciated that the following claims can be rearranged, combined, combined with other features disclosed herein, presented in multiple dependent form and the like.

What is claimed is:

1. An insertion instrument configured to insert an implant into an interspinous process space or intervertebral space, the insertion instrument comprising:
   an elongated main body having a proximal handle portion defining a central passage and a distal locking portion that selectively couples to the implant;
   a plunger slidably engaged in the central passage to fix the implant to the elongated main body;
   a proximal drive shaft operatively engaged by the proximal handle portion;
   a distal spike cap drive concentrically located partially around the plunger and the proximal drive shaft, the distal spike cap drive having a socket end configured to operatively engage the implant; and
   one or more complementary slots comprising a radial portion disposed on the proximal drive shaft, the one or more complementary slots configured to receive pins disposed on a proximal portion of the distal spike cap drive.

2. The insertion instrument of claim 1, further comprising an introducer tube, the introducer tube configured to receive a distal portion of the distal spike cap drive and the implant.

3. The insertion instrument of claim 2, wherein the one or more complementary slots are accessible to a user of the insertion instrument when the distal portion of the distal spike cap drive is received by the introducer tube.

4. The insertion instrument of claim 1, wherein the distal spike cap drive may be adjusted along a longitudinal direction according to dimensions of the one or more complementary slots, and wherein upon substantial movement of the distal spike cap drive in a proximal direction, the distal spike cap drive may be rotated in a radial direction such that the pins are received by the radial portion, placing the distal spike cap drive in a retracted configuration.

5. The insertion instrument of claim 4, wherein in the retracted configuration, the distal locking portion is exposed, thereby allowing coupling of the implant.

6. The insertion instrument of claim 1, further comprising a spring disposed concentrically around the elongated main body, the spring operatively engaging the proximal drive shaft at a first end and the distal spike cap drive at a second end, thereby biasing the distal spike cap drive in a distal direction and placing the distal spike cap drive in an extended configuration.

7. The insertion instrument of claim 6, wherein in the extended configuration, the socket end of the distal spike cap drive operatively couples to an adapter for transiently fixing the implant to the insertion instrument.

8. A surgical system comprising an implant and an insertion instrument, wherein the implant comprises:
   an elongated body having an interior and a proximal internal recess for access to the interior;
   a distal anchor comprising radially deployable blades having a first closed configuration and a second open configuration;
   a proximal anchor; and
   an actuation plunger having a proximal end and a distal end, wherein said actuation plunger is housed inside the interior of the elongated body, said distal end of the actuation plunger being operatively connected to the radially deployable blades to selectively move the radially deployable blades between the first closed configuration and the second open configuration; and wherein the insertion instrument comprises:

an elongated main body having a proximal handle portion defining a central passage and a distal locking portion that selectively couples to the implant;

a plunger slidably engaged in the central passage to fix the implant to the elongated main body;

a proximal drive shaft operatively connected to the proximal handle portion; and a distal spike cap drive concentrically located around the plunger, the distal spike cap drive comprising a socket end configured to engage an adapter, said adapter operatively engaging the implant;

wherein the distal spike cap drive defines an axial passage, and the proximal drive shaft is partially received in the axial passage.

9. The surgical system of claim 8, further comprising:

a spring substantially biasing the distal spike cap drive longitudinally away from the proximal drive shaft.

10. The surgical system of claim 8, wherein the distal spike cap drive further comprises:

one or more pins disposed at a first end directed radially inwards towards one or more complementary slots, said one or more complementary slots configured to receive a portion of the one or more pins while allowing movement therein.

11. The surgical system of claim 8, wherein the distal spike cap drive may be locked in a retracted configuration, thereby exposing the distal locking portion of the elongated main body.

12. The surgical system of claim 8, wherein the distal spike cap drive is configured to deploy the proximal anchor.

13. The surgical system of claim 8, wherein:

the distal spike cap drive further comprises a transverse locking passage; and the adapter comprises one or more locking tabs, wherein the transverse locking passage is configured to receive the one or more locking tabs of the adapter.

14. The surgical system of claim 8, wherein:

the distal spike cap drive further comprises an opening disposed at the socket end; and the adapter comprises one or more legs, wherein the opening is configured to receive the one or more legs of the adapter.

15. A method of using an insertion instrument for spinal implantation, comprising the steps:

providing the insertion instrument comprising:

a distal portion of an elongated main body received within a first axial passage defined by a proximal drive shaft;

a plunger received within a central passage of the elongated main body, wherein the distal portion of the elongated main body is received within a spring, a first end of the spring abutting the proximal drive shaft;

the distal portion of the elongated main body, the spring, and a distal segment of the proximal drive shaft received within a second axial passage defined by a distal spike cap drive, wherein one or more pins are received into one or more pin slots disposed on the distal spike cap drive; and a portion of the one or more pins are received in one or more complementary slots disposed on the proximal drive shaft, securing the distal spike cap drive thereto; and locking an implant to the insertion instrument.

16. The method of claim 15, wherein locking the implant to the insertion instrument comprises the steps:

retracting the plunger of the insertion instrument into an unlocked position;

selecting the implant and a complementary adapter for a particular amount of interspinous distraction;

retracting the distal spike cap drive into a retracted configuration;

partially engaging the implant to a tip of the elongated main body of the insertion instrument;

extending the plunger of the insertion instrument into a locked position; and extending the distal spike cap drive such that a socket end of the distal spike cap drive operatively engages the adapter.

17. The method of claim 16, wherein retracting the distal spike cap drive comprises:

biasing the distal spike cap drive proximally along the one or more complementary slots; and rotating the distal spike cap drive such that the one or more pins are received by a radial portion of the one or more complementary slots.

18. The method of claim 16, wherein extending the distal spike cap drive comprises:

rotating the distal spike cap drive; and biasing the distal spike cap drive in a distal direction via the spring.

19. The method of claim 16, further comprising receiving one or more locking tabs of the adapter into a transverse locking passage disposed on the socket end of the distal spike cap drive.

20. The method of claim 16, further comprising receiving one or more legs of the adapter into an opening disposed on the socket end of the distal spike cap drive.

* * * * *